United States Patent [19]
Kato et al.

[11] Patent Number: 6,120,663
[45] Date of Patent: Sep. 19, 2000

[54] GAS SENSOR

[75] Inventors: Nobuhide Kato, Ama-gun; Yasuhiko Hamada, Nagoya, both of Japan

[73] Assignee: NGK Insulators, Ltd., Japan

[21] Appl. No.: 09/095,605

[22] Filed: Jun. 11, 1998

[30]  Foreign Application Priority Data

Jun. 23, 1997  [JP]  Japan ................................. 9-165959

[51] Int. Cl.⁷ ............................................. G01N 27/407
[52] U.S. Cl. ...................... 204/401; 204/425; 204/426; 204/427; 205/781; 205/784.5; 205/786.5; 205/788
[58] Field of Search ........................... 204/401, 421–429; 205/781, 783.5, 784, 784.5, 785

[56]  References Cited

U.S. PATENT DOCUMENTS

| | | | |
|---|---|---|---|
| 4,167,163 | 9/1979 | Moder ...................................... | 204/424 |
| 4,609,453 | 9/1986 | Shimomura ............................... | 204/425 |
| 5,672,811 | 9/1997 | Kato et al. ................................ | 204/425 |
| 5,709,198 | 1/1998 | Sagisaka et al. ......................... | 204/401 |
| 5,763,763 | 6/1998 | Kato et al. ............................... | 204/426 |

FOREIGN PATENT DOCUMENTS

| | | |
|---|---|---|
| 0 678 740 A1 | 10/1995 | European Pat. Off. . |
| 0 849 591 A1 | 6/1998 | European Pat. Off. . |
| 196 12 387A1 | 10/1996 | Germany . |
| 58-178248 | 10/1983 | Japan . |
| 61-132851 | 6/1986 | Japan . |
| 63-38154 | 2/1988 | Japan . |
| 64-39545 | 2/1989 | Japan . |
| 1-277751 | 11/1989 | Japan . |
| 2-1543 | 1/1990 | Japan . |
| 2 194 846 | 3/1988 | United Kingdom . |
| 2 285 314 | 7/1995 | United Kingdom . |

*Primary Examiner*—T. Tung
*Attorney, Agent, or Firm*—Parkhurst & Wendel, L.L.P.

[57]  ABSTRACT

Disclosed is a gas sensor comprising a main pumping cell for pumping-processing oxygen in a first chamber; an auxiliary pumping cell for pumping-processing oxygen in a second chamber; and a measuring pumping cell for pumping-processing oxygen in a measurement gas introduced through a third diffusion rate-determining section; wherein a NOx component contained in the measurement gas is measured on the basis of a pumping current flowing through the measuring pumping cell. The gas sensor further comprises a heater for heating at least the main pumping cell, the auxiliary pumping cell, and the measuring pumping cell to predetermined temperatures; an impedance-detecting circuit for detecting an impedance between an inner pumping electrode and an auxiliary pumping electrode; and a self-diagnosis unit for comparing an impedance value detected by the impedance-detecting circuit with a prescribed value to decide whether or not any trouble occurs, on the basis of a result of comparison. Accordingly, it is possible to provide the gas sensor which has a self-diagnosis function capable of quickly and reliably detecting whether or not the gas sensor has any trouble.

10 Claims, 15 Drawing Sheets

GAS SENSOR

BACKGROUND OF THE INVENTION

1. Field of the Invention

The present invention relates to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

Various measuring systems and apparatuses have been hitherto suggested in order to know the concentration of a predetermined gas component in a measurement gas.

For example, those known as the method for measuring NOx in a measurement gas such as combustion gas include a technique in which the NOx-reducing ability of Rh is utilized while using a sensor comprising a Pt electrode and an Rh electrode formed on an oxygen ion-conductive solid electrolyte such as zirconia to measure an electromotive force generated between the both electrodes.

The sensor as described above suffers the following problem. That is, the electromotive force is greatly changed depending on the change in concentration of oxygen contained in a combustion gas as a measurement gas. Moreover, the change in electromotive force is small with respect to the change in concentration of NOx. For this reason, the conventional sensor tends to suffer influence of noise.

Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform measurement for a combustion gas produced under such a combustion condition.

A system has been disclosed, for example, in Japanese Laid-Open Patent Publication Nos. 63-38154 and 64-39545, in which a pair of electrochemical pumping cell and sensor cell comprising Pt electrode and an oxygen ion-conductive solid electrolyte are combined with another pair of electrochemical pumping cell and sensor cell comprising Rh electrode and an oxygen ion-conductive solid electrolyte to measure NOx in accordance with a difference between respective pumping current values.

Further, for example, Japanese Laid-Open Patent Publication Nos. 1-277751 and 2-1543 disclose the following method. That is, two pairs of electrochemical pumping cells and sensor cells are prepared. The limiting pumping current is measured at a partial pressure of oxygen at which NOx is not reduced, by using a sensor comprising one of the pairs of pumping cells and sensor cells, while the limiting pumping current is measured at a partial pressure of oxygen at which NOx is reduced, by using a sensor comprising the other pair of pumping cell and sensor cell so that the difference between the limiting pumping currents is determined. Besides, the difference in limiting current is measured by using a sensor comprising a pair of pumping cell and sensor cell, while switching the partial pressure of oxygen in a measurement gas between a partial pressure of oxygen at which NOx is reduced and a partial pressure of oxygen at which NOx is not reduced.

SUMMARY OF THE INVENTION

The present invention relates to the gas sensor as described above, an object of which is to provide a gas sensor which has a self-diagnosis function capable of quickly and reliably detecting whether or not the gas sensor has any trouble.

According to the present invention, there is provided a gas sensor comprising a main pumping means for pumping-processing oxygen contained in a measurement gas introduced from an external space into a processing space formed and comparted by solid electrolytes contacting with the external space so that a partial pressure of oxygen in the processing space is controlled to have a predetermined value at which a predetermined gas component as a measurement objective is not decomposable; and an electric signal-generating conversion means for making conversion into an electric signal corresponding to an amount of oxygen contained in the measurement gas after being pumping-processed by the main pumping means; wherein a measurement gas component contained in the measurement gas is measured on the basis of the electric signal supplied from the electric signal-generating conversion means; the gas sensor further comprising a heater for heating at least the main pumping means and the electric signal-generating conversion means to predetermined temperatures; an impedance-detecting means for detecting an impedance between predetermined electrodes; and a self-diagnosis means for comparing an impedance value detected by the impedance-detecting means with a prescribed value to decide whether or not any trouble occurs, on the basis of a result of comparison.

According to the present invention, at first, the oxygen, which is contained in the measurement gas introduced from the external space, is pumping-processed by the main pumping means, and the oxygen is adjusted to have a predetermined concentration. The measurement gas, which has been adjusted for the oxygen concentration by the main pumping means, is introduced into the electric signal-generating conversion means in the next step. The electric signal-generating conversion means decomposes the measurement gas component contained in the introduced measurement gas by means of catalytic action and/or electrolysis, to make conversion into the electric signal corresponding to the amount of oxygen produced by the decomposition. The measurement gas component contained in the measurement gas is measured on the basis of the electric signal supplied from the electric signal-generating conversion means.

The detecting operation described above is performed while heating at least the main pumping means and the electric signal-generating conversion means to the predetermined temperatures by the aid of the heater. Therefore, the amount of the predetermined component is detected highly accurately by using the electric signal-generating conversion means.

The predetermined gas component includes, for example, NO, and the measurement gas component includes, for example, NOx.

When the electric signal-generating conversion means comprises a measuring pumping means, the measurement gas, which has been adjusted for the oxygen concentration by the main pumping means, is introduced into the measuring pumping means.

The measuring pumping means decomposes the measurement gas component after being pumping-processed by the main pumping means, by means of catalytic action and/or electrolysis, and it pumping-processes oxygen produced by the decomposition. The predetermined gas component corresponding to an amount of oxygen is measured on the basis of a pumping current generated in the measuring pumping means in accordance with the amount of oxygen pumping-processed by the measuring pumping means.

In another embodiment, the electric signal-generating conversion means comprises a concentration-detecting means. In this case, the measurement gas, which has been adjusted for the oxygen concentration by the main pumping means, is introduced into the concentration-detecting means in the next step. An electromotive force of an oxygen concentration cell is generated in the concentration-detecting means, which corresponds to a difference between an amount of oxygen contained in a reference gas and an amount of oxygen produced by decomposition of the predetermined gas component contained in the measurement gas. The predetermined gas component corresponding to the amount of oxygen is measured on the basis of the electromotive force.

During the period in which the measurement operation is performed for the predetermined gas component, the impedance value between the predetermined electrodes is detected by the aid of the impedance-detecting means. Further, the self-diagnosis means is used to compare the impedance value with the prescribed value and decide whether or not any trouble occurs, on the basis of the result of comparison.

In general, the temperature of the gas sensor is correlated with the alternating current resistance (impedance) of the gas sensor. Specifically, the temperature of the gas sensor is proportional to the impedance of the gas sensor. Therefore, if the impedance value does not arrive at the prescribed value although the electric power is supplied to the heater, the gas sensor is out of order due to any cause (for example, disconnection of the heater or malfunction of the electrode). In the present invention, it is decided whether or not any trouble occurs in the gas sensor, by utilizing the foregoing principle.

Accordingly, the present invention makes it possible to promptly and reliably detect whether or not the gas sensor is in a failure state at present. Therefore, it is possible to make quick response to maintain and manage the gas sensor. The trouble or failure of the gas sensor includes, for example, disconnection of the heater and malfunction or abnormality of the electrode. The malfunction of the electrode is exemplified by exhaustion and peeling-off of the electrode due to thermal damage, and decrease in catalytic activity of the electrode due to, for example, poisoning and clogging.

The impedance-detecting means may detect the impedance between an electrode disposed for the main pumping means and an electrode disposed for the measuring pumping means. Alternatively, the impedance-detecting means may detect the impedance between a detecting electrode disposed for the measuring pumping means and a reference electrode exposed to a reference gas.

The impedance-detecting means may detect the impedance between an electrode disposed for the main pumping means and an electrode disposed for the concentration-detecting means. Alternatively, the impedance-detecting means may detect the impedance between a detecting electrode disposed for the concentration-detecting means and a reference electrode exposed to a reference gas.

The gas sensor according to the present invention may be constructed such that the self-diagnosis means judges that trouble occurs, when the impedance value detected by the impedance-detecting means does not arrive at the prescribed value for a predetermined period of time.

In this embodiment, the self-diagnosis means comprises a comparing means for comparing the impedance value detected by the impedance-detecting means with the prescribed value; and a monitoring means for temporarily or periodically monitoring a comparison output supplied from the comparing means and judging that trouble occurs, when the comparison output does not arrive at the prescribed value for a predetermined period of time.

The monitoring means may monitor the comparison output supplied from the comparing means for the predetermined period of time, upon completion of a predetermined condition. Alternatively, the monitoring means may monitor the comparison output supplied from the comparing means at intervals of a certain period of time for the predetermined period of time. Further alternatively, the monitoring means may be operated in accordance with a combination of the procedures described above.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Explanation will be made below with reference to FIGS. 1 to 17 for several illustrative embodiments in which the gas sensor according to the present invention is applied to gas sensors for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

Figure 1:
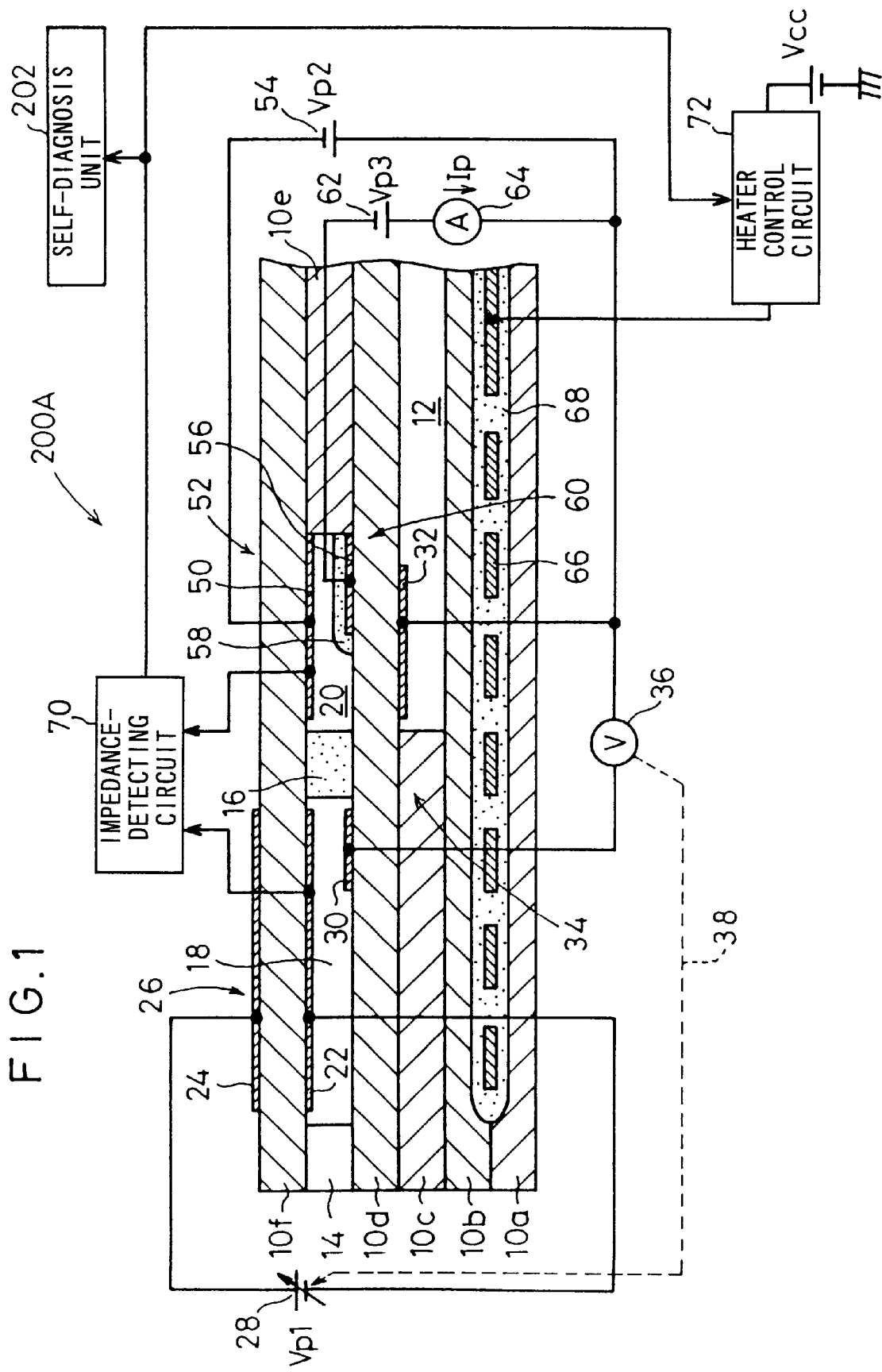
FIG. 1 shows a cross-sectional view illustrating a gas sensor according to a first embodiment.

At first, as shown in FIG. 1, a gas sensor 200A according to the first embodiment comprises, for example, six stacked solid electrolyte layers 10a to 10f composed of ceramics based on the use of oxygen ion-conductive solid electrolytes such as $ZrO_2$. First and second layers from the bottom are designated as first and second substrate layers 10a, 10b respectively. Third and fifth layers from the bottom are designated as first and second spacer layers 10c, 10e respectively. Fourth and sixth layers from the bottom are designated as first and second solid electrolyte layers 10d, 10f respectively.

Specifically, the first spacer layer 10c is stacked on the second substrate layer 10b. The first solid electrolyte layer 10d, the second spacer layer 10e, and the second solid electrolyte layer 10f are successively stacked on the first spacer layer 10c.

A space (reference gas-introducing space) 12, into which a reference gas such as atmospheric air to be used as a reference for measuring oxides is introduced, is formed between the second substrate layer 10b and the first solid electrolyte layer 10d, the space 12 being comparted by a lower surface of the first solid electrolyte layer 10d, an upper surface of the second substrate layer 10b, and side surfaces of the first spacer layer 10c.

The second spacer layer 10e is interposed between the first and second solid electrolyte layers 10d, 10f. First and second diffusion rate-determining sections 14, 16 are also interposed between the first and second solid electrolyte layers 10d, 10f.

A first chamber 18 for adjusting the partial pressure of oxygen in a measurement gas is formed and comparted by a lower surface of the second solid electrolyte layer 10f, side surfaces of the first and second diffusion rate-determining sections 14, 16, and an upper surface of the first solid electrolyte layer 10d. A second chamber 20 for finely adjusting the partial pressure of oxygen in the measurement gas and measuring oxides, for example, nitrogen oxides (NOx) in the measurement gas is formed and comparted by a lower surface of the second solid electrolyte layer 10f, a side surface of the second diffusion rate-determining section 16, a side surface of the second spacer layer 10e, and an upper surface of the first solid electrolyte layer 10d.

The external space communicates with the first chamber 18 via the first diffusion-rate determining section 14, and the first chamber 18 communicates with the second chamber 20 via the second diffusion rate-determining section 16.

The first and second diffusion-rate determining sections 14, 16 give predetermined diffusion resistances to the measurement gas to be introduced into the first and second chambers 18, 20 respectively. Each of the first and second diffusion-rate determining sections 14, 16 can be formed as a passage composed of, for example, a porous material, or a small hole having a predetermined cross-sectional area so that the measurement gas may be introduced.

Especially, the second diffusion-rate determining section 16 is arranged and filled with a porous material comprising, for example, $ZrO_2$. The diffusion resistance of the second diffusion-rate determining section 16 is made larger than the diffusion resistance of the first diffusion-rate determining section 14.

The atmosphere in the first chamber 18 is introduced into the second chamber 20 under the predetermined diffusion resistance via the second diffusion rate-determining section 16.

An inner pumping electrode 22 having a substantially rectangular planar configuration and composed of a porous cermet electrode is formed on the entire lower surface portion for forming the first chamber 18, of the lower surface of the second solid electrolyte layer 10f. An outer pumping electrode 24 is formed on a portion corresponding to the inner pumping electrode 22, of the upper surface of the second solid electrolyte layer 10f. An electrochemical pumping cell, i.e., a main pumping cell 26 is constructed by the inner pumping electrode 22, the outer pumping electrode 24, and the second solid electrolyte layer 10f interposed between the both electrodes 22, 24.

A desired control voltage (pumping voltage) Vp1 is applied between the inner pumping electrode 22 and the outer pumping electrode 24 of the main pumping cell 26 by the aid of an external variable power source 28 to allow a pumping current to flow in a positive or negative direction between the outer pumping electrode 24 and the inner pumping electrode 22. Thus, the oxygen in the atmosphere in the first chamber 18 can be pumped out to the external space, or the oxygen in the external space can be pumped into the first chamber 18.

A measuring electrode 30 having a substantially rectangular planar configuration and composed of a porous cermet electrode is formed on an upper surface portion for forming the first chamber 18 adjacent to the second diffusion rate-determining section 16, of the upper surface of the first solid electrolyte layer 10d. A reference electrode 32 is formed on a portion exposed to the reference gas-introducing space 12, of the lower surface of the first solid electrolyte layer 10d. An electrochemical sensor cell, i.e., an oxygen partial pressure-detecting cell 34 is constructed by the measuring electrode 30, the reference electrode 32, and the first solid electrolyte layer 10d.

An electromotive force is generated between the measuring electrode 30 and the reference electrode 32 on the basis of a difference in oxygen concentration between the atmosphere in the first chamber 18 and the reference gas (atmospheric air) in the reference gas-introducing space 12. The oxygen partial pressure-detecting cell 34 makes it possible to detect the partial pressure of oxygen in the atmosphere in the first chamber 18 by measuring the generated electromotive force by using a voltmeter 36.

The detected value of the partial pressure of oxygen is used to feedback-control the variable power source 28. Specifically, the pumping operation performed by the main pumping cell 26 is controlled so that the partial pressure of oxygen in the atmosphere in the first chamber 18 has a predetermined value which is sufficiently low to control the partial pressure of oxygen in the second chamber 20 in the next step.

Figure 2:
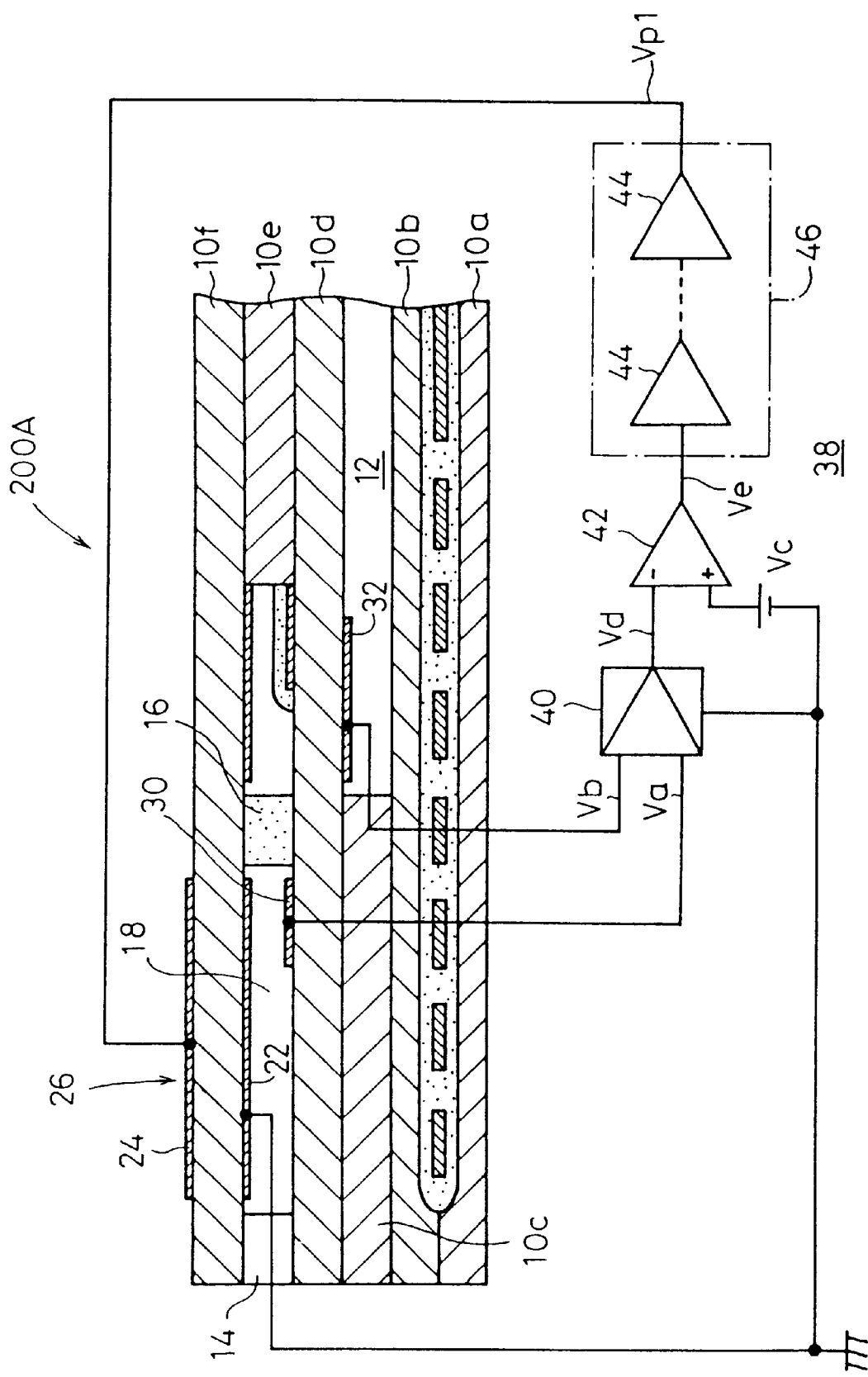
FIG. 2 shows an arrangement of a feedback control system for a main pumping cell of the gas sensor according to the first embodiment.

Specifically, as shown in FIG. 2, a circuit system (feedback control system) 38 for performing the feedback control comprises a first differential amplifier 40 for determining a difference between a difference (measured voltage Va) between an electric potential of the measuring electrode 30 and the ground electric potential and a difference (reference voltage Vb) between an electric potential of the reference electrode 32 and the ground electric potential, and amplifying the determined difference with a predetermined gain to make an output; a second differential amplifier 42 for determining a difference between the output of the first differential amplifier 40 and a reference voltage Vc, and amplifying the determined difference with a predetermined gain to make an output; and a signal-amplifying system 46 composed of a one-stage or multi-stage amplifier 44 for amplifying the output of the second differential amplifier 42 with a predetermined gain. In this embodiment, the wiring connection is made so that the output of the signal-amplifying system 46 is supplied to the outer pumping electrode 24 of the main pumping cell 26, and the inner pumping electrode 22 is grounded.

Accordingly, at first, the measurement gas is introduced into the first chamber 18 via the first diffusion rate-determining section 14. The measured voltage Va and the reference voltage Vb at that time are supplied to the first differential amplifier 40. The first differential amplifier 40 outputs the differential voltage Vd between the measured voltage Va and the reference voltage Vb. The differential voltage Vd is applied, for example, to an inverting terminal of the second differential amplifier 42 disposed at the downstream stage. The second differential amplifier 42 determines the difference between the differential voltage Vd supplied to the inverting terminal and the reference voltage Vc supplied to a non-inverting terminal. The voltage signal Ve, which is obtained by amplifying the determined difference with the predetermined gain, is outputted from an output terminal of the second differential amplifier 42. The voltage signal Ve is amplified with the predetermined gain by the signal-amplifying system 46 disposed at the downstream stage, and an obtained voltage is supplied as the pumping voltage Vp1 to the outer pumping electrode 24 of the main pumping cell 26. In this embodiment, the inner pumping electrode 22 has the ground electric potential (0 V). Therefore, the voltage between the both electrodes 22, 24 of the main pumping cell 26 is equivalent to the pumping voltage Vp1 supplied from the signal-amplifying system 46 after all.

Therefore, the main pumping cell 26 pumps out or pumps in oxygen in an amount corresponding to the level of the pumping voltage Vp1, of the measurement gas introduced into the first chamber 18. The oxygen concentration in the first chamber 18 is subjected to feedback control to give a predetermined level by repeating the series of operations described above.

The porous cermet electrode for constructing the inner pumping electrode 22 and the outer pumping electrode 24 is composed of a metal such as Pt and a ceramic such as $ZrO_2$. However, it is necessary, for the inner pumping electrode 22 and the measuring electrode 30 arranged in the first chamber 18 contacting with the measurement gas, to use a material having a weak reducing ability or no reducing ability with respect to the NO component in the measurement gas. It is preferable that the inner pumping electrode 22 and the measuring electrode 30 are composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

On the other hand, as shown in FIG. 1, an auxiliary pumping electrode 50 having a substantially rectangular planar configuration and composed of a porous cermet electrode is formed on the entire lower surface portion for forming the second chamber 20, of the lower surface of the second solid electrolyte layer 10f. An auxiliary electrochemical pumping cell, i.e., an auxiliary pumping cell 52 is constructed by the auxiliary pumping electrode 50, the reference electrode 32, the second solid electrolyte layer 10f, the second spacer layer 10e, and the first solid electrolyte layer 10d.

A desired constant voltage Vp2 is applied between the reference electrode 32 and the auxiliary pumping electrode 50 of the auxiliary pumping cell 52 by the aid of an external power source 54. Thus, the oxygen in the atmosphere in the second chamber 20 can be pumped out to the reference gas-introducing space 12. Accordingly, the partial pressure of oxygen in the atmosphere in the second chamber 20 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 26 for the first chamber 18, the change in amount of oxygen introduced into the second chamber 20 is greatly reduced as compared with the change in the measurement gas. Accordingly, the partial pressure of oxygen in the second chamber 20 is accurately controlled to be constant.

In the gas sensor 200A according to the first embodiment, a detecting electrode 56 having a substantially rectangular planar configuration and composed of a porous cermet electrode is formed at a portion separated from the second diffusion rate-determining section 16, on an upper surface portion for forming the second chamber 20, of the upper surface of the first solid electrolyte layer 10d. An alumina film for constructing a third diffusion rate-determining section 58 is formed so that the detecting electrode 56 is covered therewith. An electrochemical pumping cell, i.e., a measuring pumping cell 60 is constructed by the detecting electrode 56, the reference electrode 32, and the first solid electrolyte layer 10d.

The detecting electrode 56 is composed of a porous cermet comprising zirconia as a ceramic and Rh as a metal capable of reducing NOx as the measurement gas component. Accordingly, the detecting electrode 56 functions as a NOx-reducing catalyst for reducing NOx existing in the atmosphere in the second chamber 20. Further, the oxygen in the atmosphere in the second chamber 20 can be pumped out to the reference gas-introducing space 12 by applying a constant voltage Vp3 between the detecting electrode 56 and the reference electrode 32 by the aid of a DC power source 62. The pumping current Ip, which is allowed to flow in accordance with the pumping operation performed by the measuring pumping cell 60, is detected by an ammeter 64.

The constant voltage (DC) power source 62 can apply a voltage of a magnitude to give a limiting current to the pumping for oxygen produced during decomposition in the measuring pumping cell 60 under the inflow of NOx restricted by the third diffusion rate-determining section 58.

The gas sensor 200A according to the first embodiment further comprises a heater 66 for generating heat in accordance with electric power supply from the outside. The heater 66 is embedded in a form of being vertically interposed between the first and second substrate layers 10a, 10b. The heater 66 is provided in order to increase the conductivity of oxygen ion. A ceramic layer 68 composed of alumina or the like is formed to cover upper and lower surfaces of the heater 66 so that the heater 66 is electrically insulated from the substrate layers 10a, 10b.

As shown in FIG. 1, the heater 66 is arranged over the entire portion ranging from the first chamber 18 to the second chamber 20. Accordingly, each of the first chamber 18 and the second chamber 20 is heated to a predetermined temperature. Simultaneously, each of the main pumping cell 26, the oxygen partial pressure-detecting cell 34, the auxiliary pumping cell 52, and the measuring pumping cell 60 is also heated to a predetermined temperature and maintained at that temperature.

The gas sensor 200A according to the first embodiment includes a heater control system comprising an impedance-detecting circuit 70 inserted and connected between, for example, the inner pumping electrode 22 of the main pumping cell 26 and the auxiliary pumping electrode 50 for detecting the impedance between the both electrodes 22, 50, and a heater control circuit 72 for controlling electric power application to the heater 66 on the basis of a detection signal supplied from the impedance-detecting circuit 70.

Figure 3:
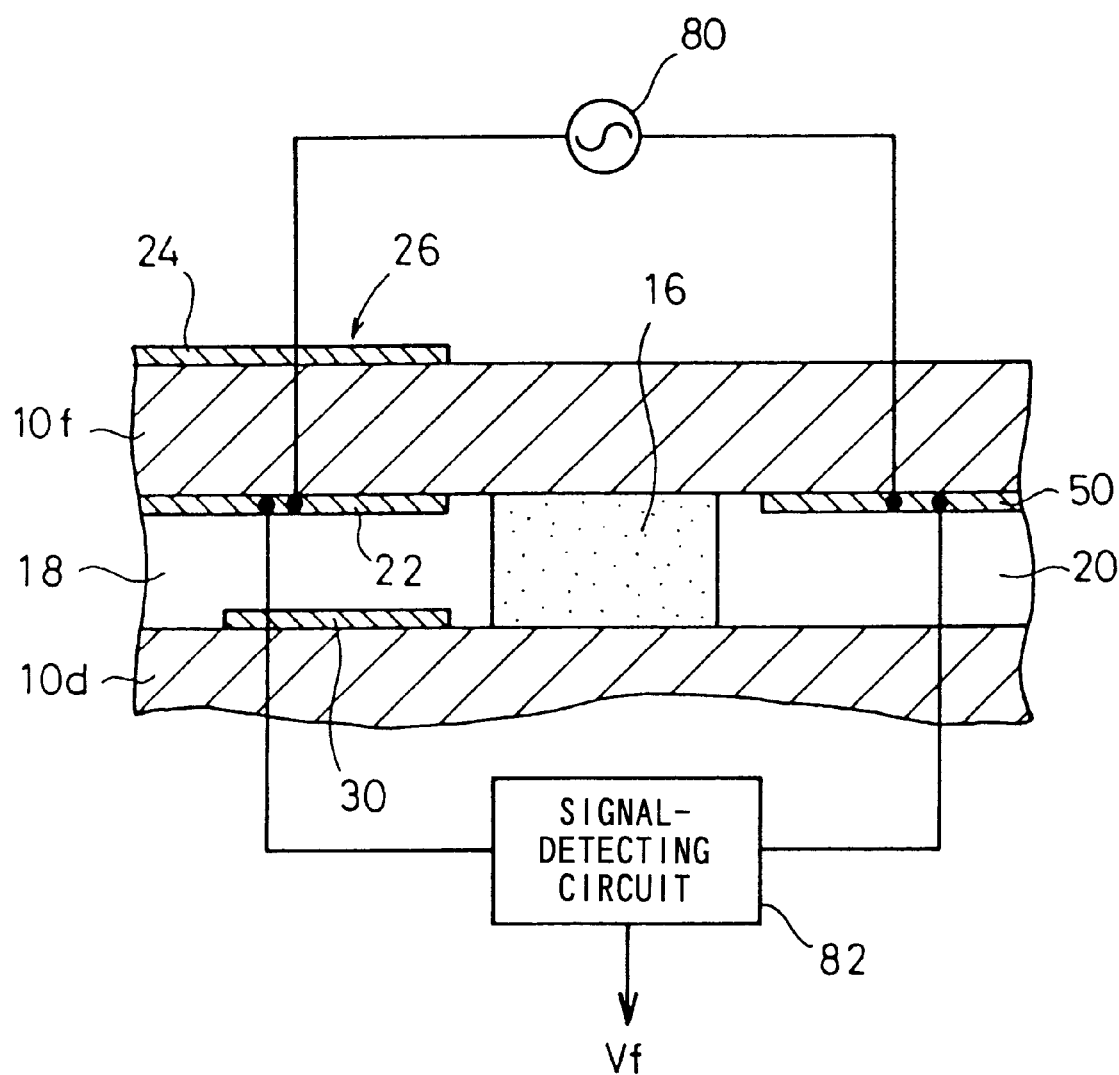
FIG. 3 shows a heater control system of the gas sensor according to the first embodiment.

As shown in FIG. 3, the impedance-detecting circuit 70 includes an alternating current-generating circuit 80 for supplying an alternating current between the inner pumping electrode 22 and the auxiliary pumping electrode 50, and a signal-detecting circuit 82 for detecting a voltage signal Vf at a level corresponding to the impedance between the electrodes 22, 50, generated between the electrodes 22, 50 in accordance with the alternating current supply between the electrodes 22, 50.

Figure 4:
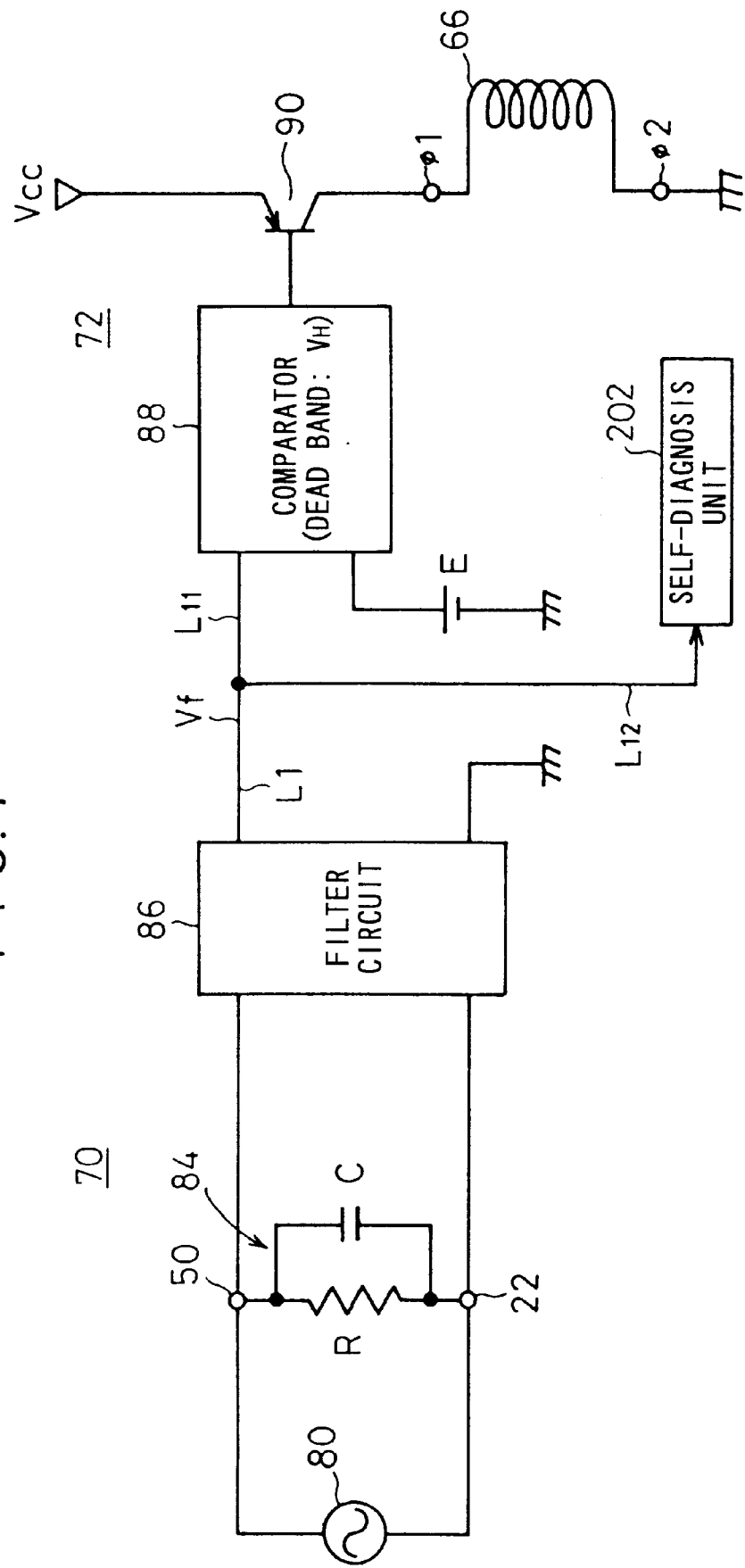
FIG. 4 shows a circuit diagram illustrating a specified example of the heater control system.

As shown in FIG. 4, the impedance measurement objective, which is constructed by the inner pumping electrode 22, the auxiliary pumping electrode 50, and the second solid electrolyte layer 10f interposed between the both electrodes 22, 50, is equivalently represented by a circuit 84 comprising a resistor R and a capacitor C connected in parallel.

Therefore, as shown in FIG. 4, the signal-detecting circuit 82 may be constructed by a filter circuit (for example, a low-pass filter and a band-pass filter) 86 for converting the alternating current signal generated between the electrodes 22, 50 into the voltage signal Vf at a level corresponding to the impedance between the electrodes 22, 50.

On the other hand, as also shown in FIG. 4, the heater control circuit 72 is constructed as having a comparator 88 with hysteresis, and a pnp-type power transistor 90. The comparator 88 with hysteresis is operated as follows. That is, assuming that the reference level is E, and the dead band level is $V_H$, if the level of the voltage signal Vf outputted from the filter circuit 86 is higher than a positive threshold level $(E+V_H/2)$, then a low level signal is outputted, while if the detection level is lower than a negative threshold level $(E-V_H/2)$, then a high level signal is outputted. If the detection level is within a range of $-V_H/2$ to $+V_H/2$, the present level is maintained.

The power transistor 90 has its collector terminal to which a power source Vcc is connected, its base terminal to which an output side of the comparator 88 with hysteresis is connected, and its emitter terminal to which a first terminal φ1 of the heater 66 is connected. A second terminal φ2 of the heater 66 is grounded.

The power transistor 90 is ON-operated by supplying the low level signal from the comparator 88 to the base terminal. Accordingly, the driving current is supplied from the power source Vcc to the heater 66. On the other hand, the power transistor 90 is OFF-operated by supplying the high level signal from the comparator 88 to the base terminal. Accordingly, the supply of the driving current to the heater 66 is stopped.

The frequency band of the alternating current component generated by the alternating current-generating circuit 80 is desirably set, for example, to be within a range of about 300 Hz to 100 kHz, and optimally within a range of 1 kHz to 10 kHz. The voltage of the alternating current component is desirably set to be at a level at which no trouble occurs in the function of each electrode, for example, not more than 500 mV, and optimally about 100 mV to 300 mV.

The reference level E, which is supplied to the comparator 88 of the heater control circuit 72, is set to be the same level as the detection level obtained when the temperature of the measurement gas in the sensor element is at a predetermined temperature (desired temperature).

The operation of the gas sensor 200A will now be explained. At first, the forward end of the gas sensor 200A is disposed in the external space. Accordingly, the measurement gas is introduced into the first chamber 18 under the predetermined diffusion resistance via the first diffusion rate-determining section 14. The measurement gas, which has been introduced into the first chamber 18, is subjected to the pumping operation for oxygen, caused by applying the predetermined pumping voltage Vp1 between the outer pumping electrode 24 and the inner pumping electrode 22 which construct the main pumping cell 26. The partial pressure of oxygen is controlled to be a predetermined value, for example, $10^{-7}$ atm. The control is performed by the aid of the feedback control system 38 shown in FIG. 2.

The first diffusion rate-determining section 14 serves to limit the amount of diffusion and inflow of oxygen in the measurement gas into the measuring space (first chamber 18) when the pumping voltage Vp1 is applied to the main pumping cell 26 so that the current flowing through the main pumping cell 26 is suppressed.

In the first chamber 18, a state of partial pressure of oxygen is established, in which NOx in the atmosphere is not reduced by the inner pumping electrode 22 and the measuring electrode 30 in an environment of being heated by the external measurement gas and being heated by the heater 66. For example, a condition of partial pressure of oxygen is formed, in which the reaction of NO→½$N_2$+½$O_2$ does not occur, because of the following reason. That is, if NOx in the measurement gas (atmosphere) is reduced in the first chamber 18, it is impossible to accurately measure NOx in the second chamber 20 disposed at the downstream. Therefore, it is necessary to establish a condition in the first chamber 18 in which NOx is not reduced by the component which participates in reduction of NOx (in this case, the metal component of the inner pumping electrode 22 and the measuring electrode 30). Specifically, such a condition is achieved by using, for the inner pumping electrode 22 and the measuring electrode 30, a material having a low ability to reduce NOx, for example, an alloy of Au and Pt.

The gas in the first chamber 18 is introduced into the second chamber 20 under the predetermined diffusion resistance via the second diffusion rate-determining section 16. The gas, which has been introduced into the second chamber 20, is subjected to the pumping operation for oxygen, caused by applying the predetermined constant voltage Vp2 between the reference electrode 32 and the auxiliary pumping electrode 50 which constitute the auxiliary pumping cell 52 to make fine adjustment so that the partial pressure of oxygen has a constant and low value of partial pressure of oxygen.

The second diffusion rate-determining section 16 serves to limit the amount of diffusion and inflow of oxygen in the measurement gas into the measuring space (second chamber 20) when the constant voltage Vp2 is applied to the auxiliary pumping cell 52 so that the current flowing through the auxiliary pumping cell 52 is suppressed, in the same manner as performed by the first diffusion rate-determining section 14.

In the second chamber 20, a state of partial pressure of oxygen is also established, in which NOx in the atmosphere is not reduced by the auxiliary pumping electrode 50 in an environment of being heated by the external measurement gas and being heated by the heater 66, in the same manner as established in the first chamber 18. Accordingly, it is also necessary for the auxiliary pumping electrode 50 to use a material having a weak reducing ability or no reducing ability with respect to the NO component in the measurement gas, in the same manner as the inner pumping electrode 22 and the measuring electrode 30. It is preferable that the auxiliary pumping electrode 50 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

The measurement gas, which has been controlled for the partial pressure of oxygen in the second chamber 20 as described above, is introduced into the detecting electrode 56 under the predetermined diffusion resistance via the third diffusion rate-determining section 58.

When it is intended to control the partial pressure of oxygen in the atmosphere in the first chamber 18 to have a low value of the partial pressure of oxygen which does not substantially affect the measurement of NOx, by operating the main pumping cell 26, in other words, when the pumping voltage Vp1 of the variable power source 28 is adjusted by the aid of the feedback control system 38 so that the voltage detected by the oxygen partial pressure-detecting cell 34 is constant, if the oxygen concentration in the measurement gas greatly changes, for example, in a range of 0 to 20%, then the respective partial pressures of oxygen in the atmosphere in the second chamber 20 and in the atmosphere in the vicinity of the detecting electrode 56 slightly change in ordinary cases. This phenomenon is caused probably because of the following reason. That is, when the oxygen concentration in the measurement gas increases, the distribution of the oxygen concentration occurs in the widthwise direction and the thickness direction over the measuring electrode 30 in the first chamber 18. The distribution of the oxygen concentration changes depending on the oxygen concentration in the measurement gas.

However, in the case of the gas sensor 200A according to the first embodiment, the auxiliary pumping cell 52 is provided for the second chamber 20 so that the partial pressure of oxygen in its internal atmosphere always has a constant low value of the partial pressure of oxygen. Accordingly, even when the partial pressure of oxygen in the atmosphere introduced from the first chamber 18 into the second chamber 20 changes depending on the oxygen concentration in the measurement gas, the partial pressure of oxygen in the atmosphere in the second chamber 20 can be always made to have a constant low value, owing to the pumping operation performed by the auxiliary pumping cell 52. As a result, the partial pressure of oxygen can be controlled to have a low value at which the measurement of NOx is not substantially affected.

NOx in the measurement gas introduced into the detecting electrode 56 is reduced or decomposed around the detecting electrode 56. Thus, for example, a reaction of $NO \rightarrow \frac{1}{2}N_2 + \frac{1}{2}O_2$ is allowed to occur. In this process, a predetermined voltage Vp3, for example, 430 mV (700° C.) is applied between the detecting electrode 56 and the reference electrode 32 for constructing the measuring pumping cell 60, In a direction to pump out the oxygen from the second chamber 20 to the reference gas-introducing space 12.

Therefore, the pumping current Ip flowing through the measuring pumping cell 60 has a value which is proportional to a sum of the oxygen concentration in the atmosphere introduced into the second chamber 20, i.e., the oxygen concentration in the second chamber 20 and the oxygen concentration produced by reduction or decomposition of NOx by the aid of the detecting electrode 56.

In this embodiment, the oxygen concentration in the atmosphere in the second chamber 20 is controlled to be constant by means of the auxiliary pumping cell 52. Accordingly, the pumping current Ip flowing through the measuring pumping cell 60 is proportional to the NOx concentration. The NOx concentration corresponds to the amount of diffusion of NOx limited by the third diffusion rate-determining section 58. Therefore, even when the oxygen concentration in the measurement gas greatly changes, it is possible to accurately measure the NOx concentration, based on the use of the measuring pumping cell 60 by the aid of the ammeter 64.

It is assumed, for example, that the partial pressure of oxygen in the atmosphere in the second chamber 20 controlled by the auxiliary pumping cell 52 is 0.02 ppm, and the concentration of NO as the NOx component in the measurement gas is 100 ppm. The pumping current Ip flows in an amount corresponding to a sum (=50.02 ppm) of an oxygen concentration of 50 ppm produced by reduction or decomposition of NO and the oxygen concentration of 0.02 ppm in the atmosphere in the second chamber 20. Therefore, almost all of the pumping current value obtained by operating the measuring pumping cell 60 represents the amount brought about by the reduction or decomposition of NO. Accordingly, the obtained result does not depend on the oxygen concentration in the measurement gas.

During the period in which the foregoing operation is performed, the impedance between the inner pumping electrode 22 and the auxiliary pumping electrode 50 is detected as a voltage level by the aid of the impedance-detecting circuit 70. The electric power application to the heater 66 is controlled on the basis of the detected voltage level by the aid of the heater control circuit 72.

Specifically, if the temperature of the measurement gas becomes lower than the predetermined temperature, and the impedance between the electrodes 22, 50 is increased, then the level of the voltage signal Vf outputted from the filter circuit 86 (see FIG. 4) of the impedance-detecting circuit 70 is also increased. If the level of the voltage signal Vf becomes higher than the positive threshold level $(E+V_H/2)$ of the comparator 88, then the low level signal is supplied to the base electrode of the power transistor 90 included in the heater control circuit 72, and the electric power application to the heater 66 is started. Accordingly, the temperature of the measurement gas in the sensor element is gradually increased.

On the other hand, if the temperature of the measurement gas becomes higher than the predetermined temperature, and the impedance between the electrodes 22, 50 is decreased, then the level of the voltage signal Vf outputted from the filter circuit 86 is also decreased. If the level of the voltage signal Vf becomes lower than the negative threshold level $(E-V_H/2)$ of the comparator 88, then the high level signal is supplied to the base electrode of the power transistor 90 included in the heater control circuit 72, and the electric power application to the heater 66 is stopped. Accordingly, the temperature of the measurement gas in the sensor element is gradually decreased. As described above, the temperature in the sensor element can be maintained to be constant by controlling the electric power application to the heater 66 on the basis of the impedance value.

Accordingly, it is unnecessary for the gas sensor 200A according to the first embodiment to manufacture the gas sensor 200A as having a strict resistance ratio between the resistance value of the lead section of the heater and the resistance value of the heat-generating section of the heater. Further, it is possible to avoid the influence which would be otherwise exerted by the temperature of the measurement gas due to the increase in resistance value of the heater lead section.

In the gas sensor 200A according to the first embodiment, the impedance value between the electrodes is detected. Therefore, the voltage Vp3 applied to the measuring pumping cell 60 is free from variation which would be otherwise caused by the detection of the impedance. Accordingly, it is possible to suppress, for example, superimposition of noise and fluctuation of the pumping current Ip detected by the aid of the ammeter 64. In other words, it is possible to suppress variation of the detection output which would be otherwise caused depending on the temperature of the measurement gas. Further, it is possible to realize a high S/N ratio of the detection output.

As shown in FIG. 1, the gas sensor 200A according to the first embodiment includes a self-diagnosis unit 202 for monitoring the condition of the gas sensor 200A, connected downstream from the impedance-detecting circuit 70.

Specifically, as shown in FIG. 4, an output line L1 of the filter circuit 86 is branched into two. One output line $L_{11}$ is connected to the comparator 88 with hysteresis, and the other output line $L_{12}$ is connected to the self-diagnosis unit 202.

Figure 5:
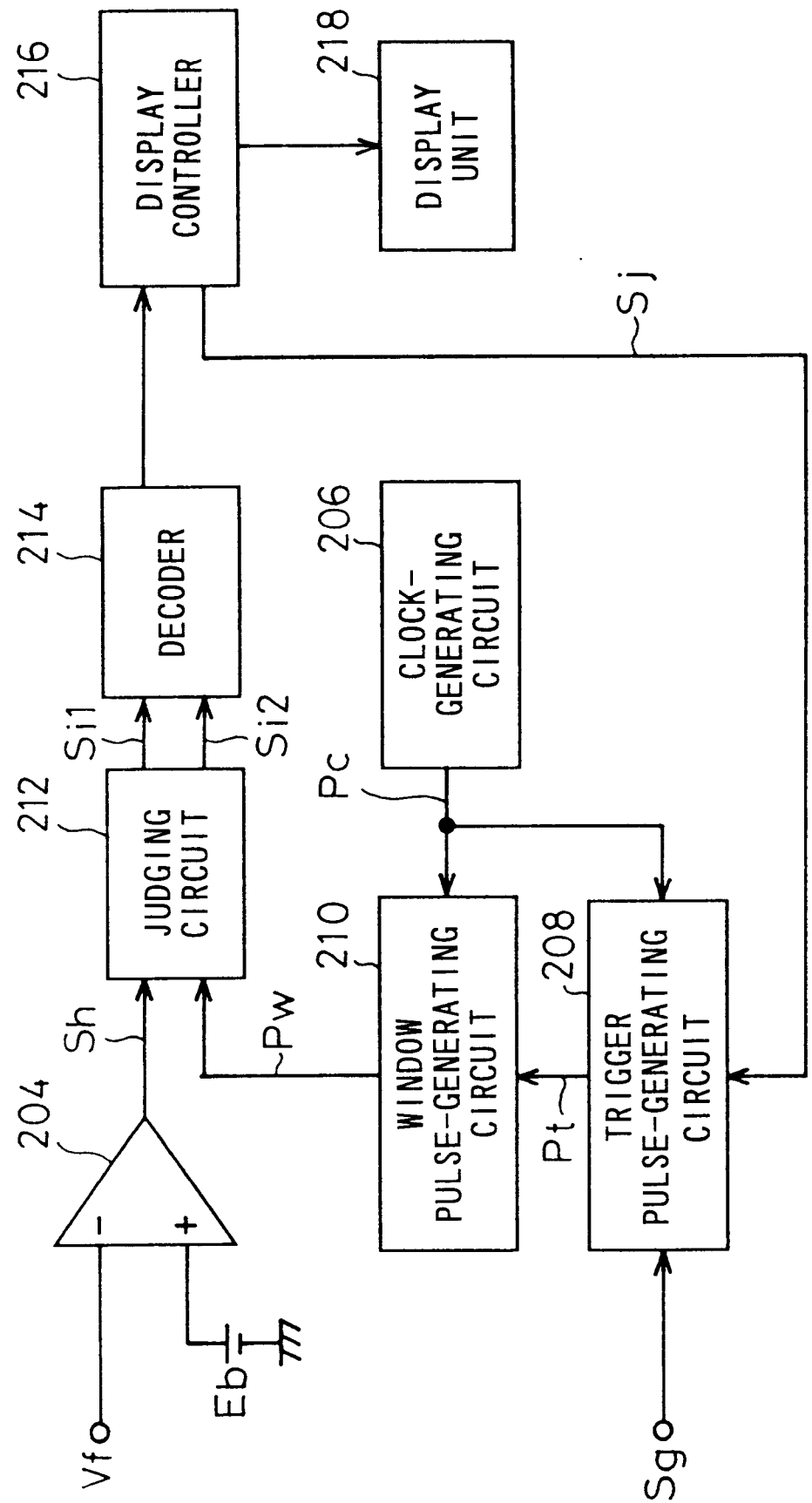
FIG. 5 shows a block diagram illustrating a specified example of a self-diagnosis unit connected to the gas sensor according to the first embodiment.

As shown in FIG. 5, the self-diagnosis unit 202 comprises a comparator 204 for comparing the level of the voltage signal Vf supplied from the filter circuit 86 with a prescribed level Eb, a clock-generating unit 206 for generating a predetermined clock Pa, a trigger pulse-generating circuit 208 for generating a trigger pulse signal Pt on the basis of an input of an instruction signal Sg supplied, for example, from an unillustrated microcomputer installed outside, a window pulse-generating circuit 210 for generating a window pulse Pw having a predetermined pulse width on the basis of an input of the trigger pules signal Pt supplied from the trigger pulse-generating circuit 208, a judging circuit 212 for judging whether or not the level of the voltage signal Vf arrives at the prescribed level Eb within the pulse width of the window pulse Pw outputted from the window pulse-generating circuit 210, a decoder 214 for analyzing a result of judgement supplied from the judging circuit 212 to make an output as a display control signal, and a display controller 216 for outputting, to a display unit 218, a display signal or display data corresponding to an attribute of the control signal supplied from the decoder 214.

Figure 6:
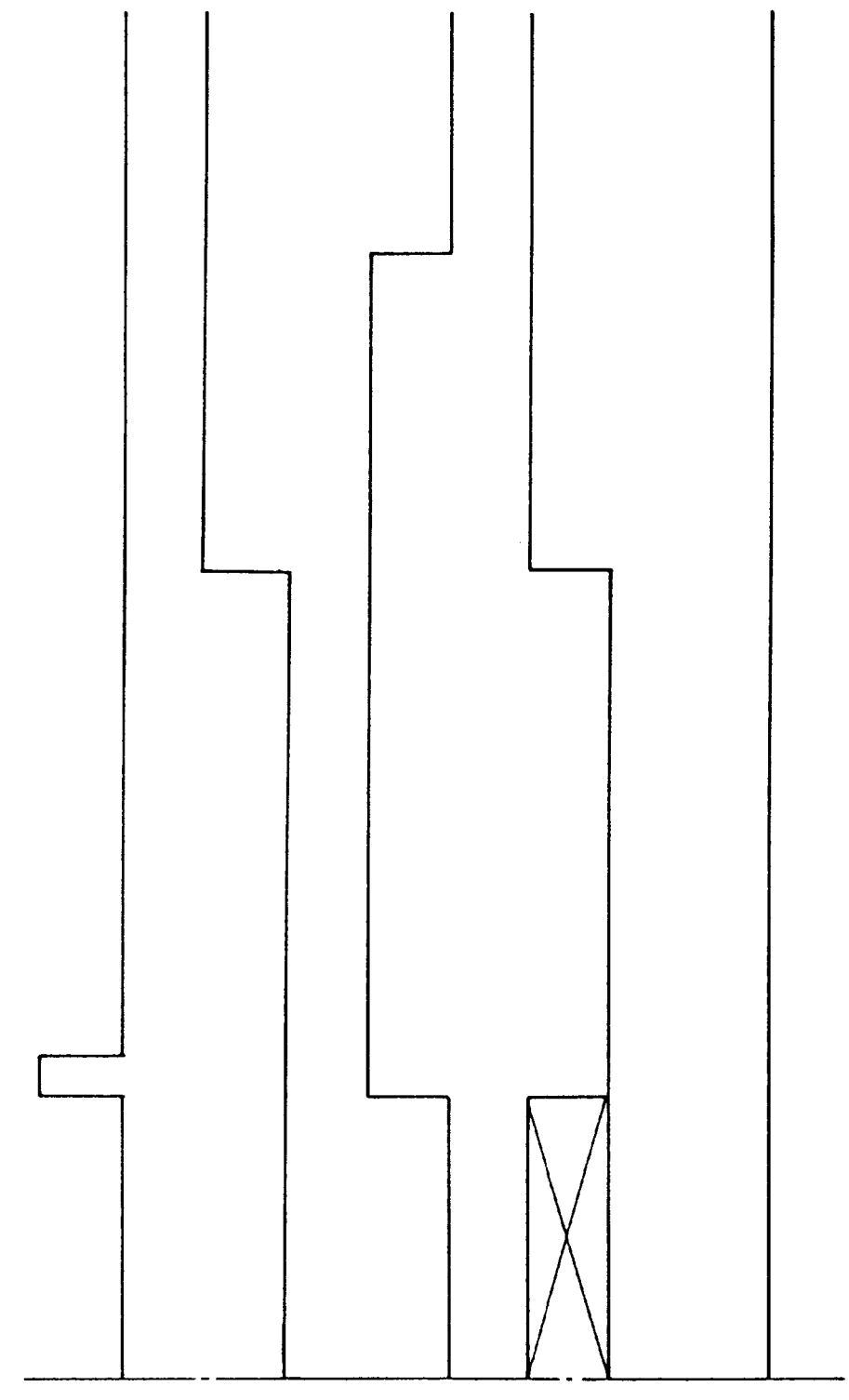
FIG. 6 shows a timing chart illustrating an example of signal processing effected by the self-diagnosis unit when the gas sensor is normally operated.

The comparator 204 outputs, for example, a high level signal Sh if the level of the voltage signal Vf is higher than the prescribed level Eb, while it outputs a low level signal Sh if the level of the voltage signal Vf is lower than the prescribed level Eb (see FIG. 6).

The trigger pulse-generating circuit 208 is in an enable state, for example, on the basis of the input of the instruction signal Sg from the outside, and it generates one trigger pulse Pt, for example, at an initial rising timing of an clock Pc. Thereafter, the trigger pulse-generating circuit 208 generates the trigger pulse Pt every time when a predetermined number of clocks are counted.

Figure 7:
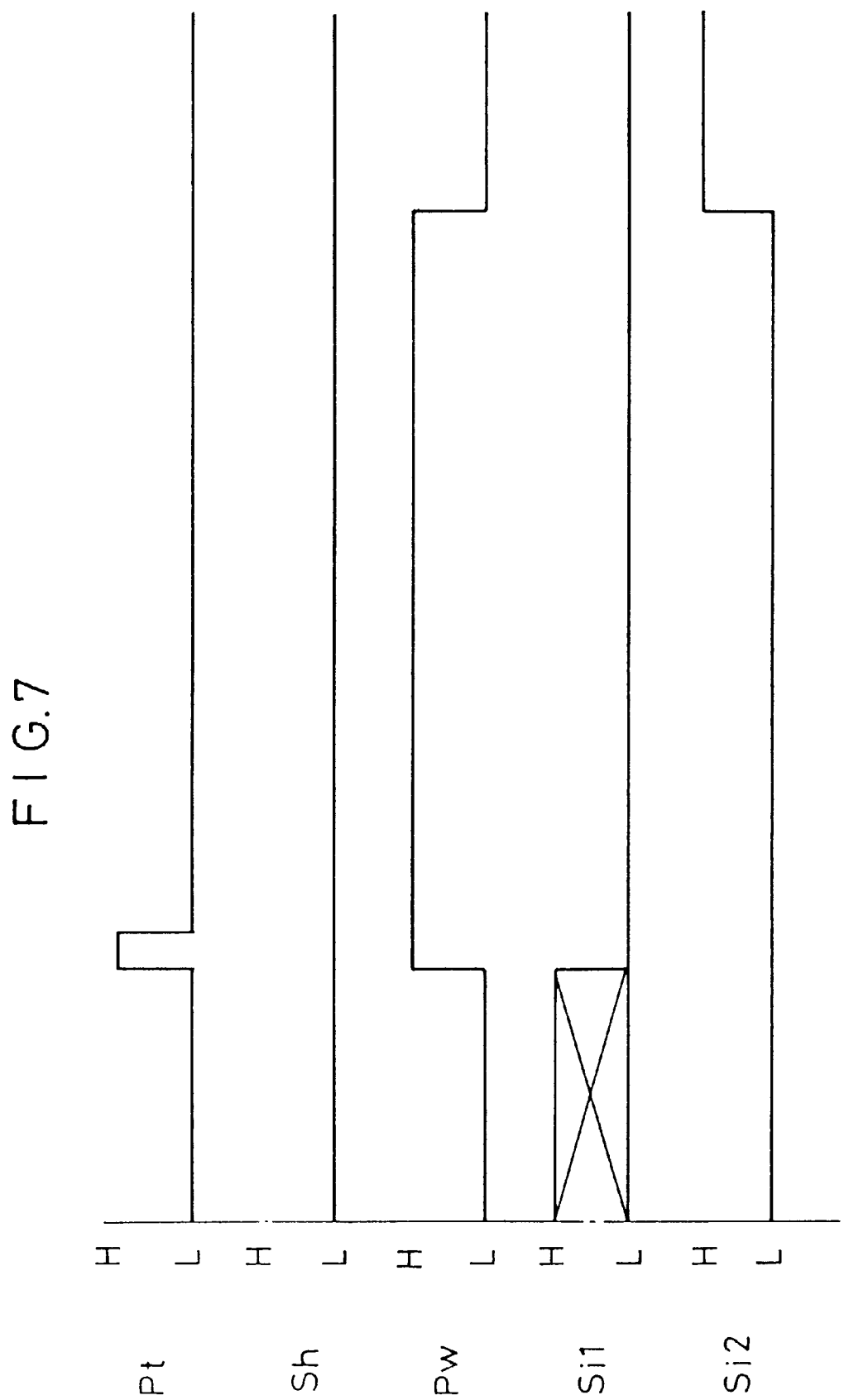
FIG. 7 shows a timing chart illustrating an example of signal processing effected by the self-diagnosis unit when the gas sensor is abnormally operated.

The window pulse-generating circuit 210 is in an enable state on the basis of the input of the trigger pulse Pt supplied from the trigger pulse-generating circuit 208, and it generates, for example, one window pulse Pw which rises at the initial rising timing of the clock Pc and which falls at a point of time at which a predetermined number of clocks are counted (see FIGS. 6 and 7).

The judging circuit 212 outputs two types of judgement signals (first and second judgement signals Si1, Si2) depending on the change in level of the window pulse Pw and the output signal Sh from the comparator 204.

As shown in FIG. 6, for example, the first judgement signal Si1 is at a low level if the output signal Sh from the comparator 204 is at a high level at the point of time of rising of the window pulse Pw, and it is at a high level if the output signal Sh from the comparator 204 is at a low level within the pulse width of the window pulse Pw. Therefore, if the output signal from the comparator 204 is not at the low level within the pulse width of the window pulse Pw, that is, if the level of the voltage signal Vf does not become higher than the prescribed level Eb, then the first judgement signal Si1 maintains the low level.

As shown in FIG. 7, for example, the second judgement signal Si2 is at the high level at the point of time of completion of the window pulse Pw (at the point of falling thereof) if the first judgement signal Si1 is at the low level.

The decoder 214 outputs a control signal (for example, a low level signal) for indicating "normal" to the display controller 216 disposed downstream if the first and second judgement signals Si1, Si2 are at the high level and the low level respectively. The decoder 214 outputs a control signal (for example, a high level signal) for indicating "abnormal" to the display controller 216 disposed downstream if the first and second judgement signals Si1, Si2 are at the low level and the high level respectively.

The display controller 216 outputs, to the display unit 218 disposed downstream, information indicating "normal", for example, display data for message or symbol to indicate "normal" if the control signal fed from the decoder 214 indicates "normal". When the display unit 218 is, for example, an LED (light emitting diode), the display controller 216 outputs, for example, a signal indicating light-out.

On the other hand, the display controller 216 outputs information indicating "abnormal", for example, display data for message or symbol to indicate "abnormal" if the control signal fed from the decoder 214 indicates "abnormal". When the display unit 218 is, for example, an LED (light emitting diode), the display controller 216 outputs, for example, a signal indicating light-up.

If the control signal indicating "abnormal" is supplied from the decoder 214 disposed upstream, the display controller 216 outputs a disable signal Sj to the trigger pulse-generating circuit 208 so that the trigger pulse-generating circuit 208 is in a stopped state.

The gas sensor 200A according to the first embodiment is basically constructed as described above. Next, its function and effect, especially function and effect of the self-diagnosis unit 202 will be explained.

At first, when the power source is turned on for the apparatus installed with the gas sensor 200A, the initial operation is performed in the apparatus. The initial operation includes electric power application to the heater 66 of the gas sensor 200A.

At a point of time after passage of a predetermined period of time (for example, a period of time for completing the warming-up process for the gas sensor 200A) from the point of time of the electric power application to the heater 66, the microcomputer (not shown) outputs the instruction signal Sg to the trigger pulse-generating circuit 208 of the self-diagnosis unit 202. When the apparatus for installing the gas sensor 200A therein is an automobile, the point of time of the completion of the warming-up process indicates a point of time at which the water temperature arrives at a predetermined value.

From the point of time at which the instruction signal Sg is supplied from the microcomputer (not shown) to the self-diagnosis unit 202, the self-diagnosis unit 202 starts monitoring for the gas sensor 200A, i.e., monitoring for the impedance value (impedance value between the inner pumping electrode 22 and the auxiliary pumping electrode 50) supplied from the impedance-detecting circuit 70. In this embodiment, the monitoring is performed for the level of the voltage signal Vf obtained by converting the impedance value into the voltage.

As shown in FIG. 6, if the impedance value from the impedance-detecting circuit 70 (level of the voltage signal Vf) arrives at the prescribed value (prescribed level) Eb within the predetermined period of time (within the pulse width of the window pulse Pw), the first and second judgement signals Si1, Si2 outputted from the judging circuit 212 are at the high level and the low level respectively. Therefore, the control signal indicating "normal" is outputted from the decoder 214. As a result, the display unit 218 makes a display indicating "normal".

After that, the instruction signal Sg is periodically supplied from the microcomputer (not shown) to the self-diagnosis unit 202. Self-diagnosis for the gas sensor 200A is performed every time when the instruction signal Sg is supplied.

On the other hand, as shown in FIG. 7, if the level of the voltage signal Vf does not arrive at the prescribed level Eb even after passage of the predetermined period of time, the judging circuit 212 outputs the fist judgement signal Si1 at the low level and the second judgement signal Si2 at the high level respectively. Accordingly, the control signal indicating "abnormal" is outputted from the decoder 214, and the display unit 218 makes a display indicating "abnormal". Upon the judgement of abnormality, the disable signal Sj is outputted from the display controller 216 to the trigger pulse-generating circuit 208. The process for judging the trouble to be performed by the self-diagnosis unit 202 thereafter is completed. The display indicating "abnormal" is made until the reset input is made for the display unit 218.

In general, the temperature of the gas sensor 200A is correlated with the alternating current resistance (impedance) of the gas sensor 200A. Specifically, the temperature of the gas sensor 200A is proportional to the impedance of the gas sensor 200A. Therefore, if the impedance value (for example, the impedance value between the inner pumping electrode 22 and the auxiliary pumping electrode 50) does not arrive at the prescribed value Eb although the electric power is supplied to the heater 66, the gas sensor 200A has any trouble due to any cause (for example, disconnection of the heater 66 or malfunction of the electrode). The self-diagnosis unit 202 of the gas sensor 200A according to the first embodiment decides whether or not any trouble occurs in the gas sensor 200A by utilizing the foregoing principle.

As a result, in the gas sensor 200A according to the first embodiment, it is possible to promptly and reliably detect whether or not the gas sensor 200A is in a failure state at present. Therefore, it is possible to make quick response to maintain and manage the gas sensor 200A (including response to legislation).

The trouble or failure of the gas sensor 200A includes, for example, disconnection of the heater 66 and malfunction of the electrode. The malfunction of the electrode is exemplified by exhaustion and peeling-off of the electrode due to thermal damage, and decrease in catalytic activity of the electrode due to, for example, poisoning and clogging.

Next, three modified embodiments of the gas sensor 200A according to the first embodiment will be described with reference to FIGS. 8 to 17. Components or parts corresponding to those shown in FIGS. 1 and 4 are designated by the same reference numerals, duplicate explanation of which will be omitted.

At first, a gas sensor according to the first modified embodiment is constructed in approximately the same manner as the gas sensor 200A according to the first embodiment. However, the former is different from the latter in the arrangement of the heater control system as follows.

Figure 8:
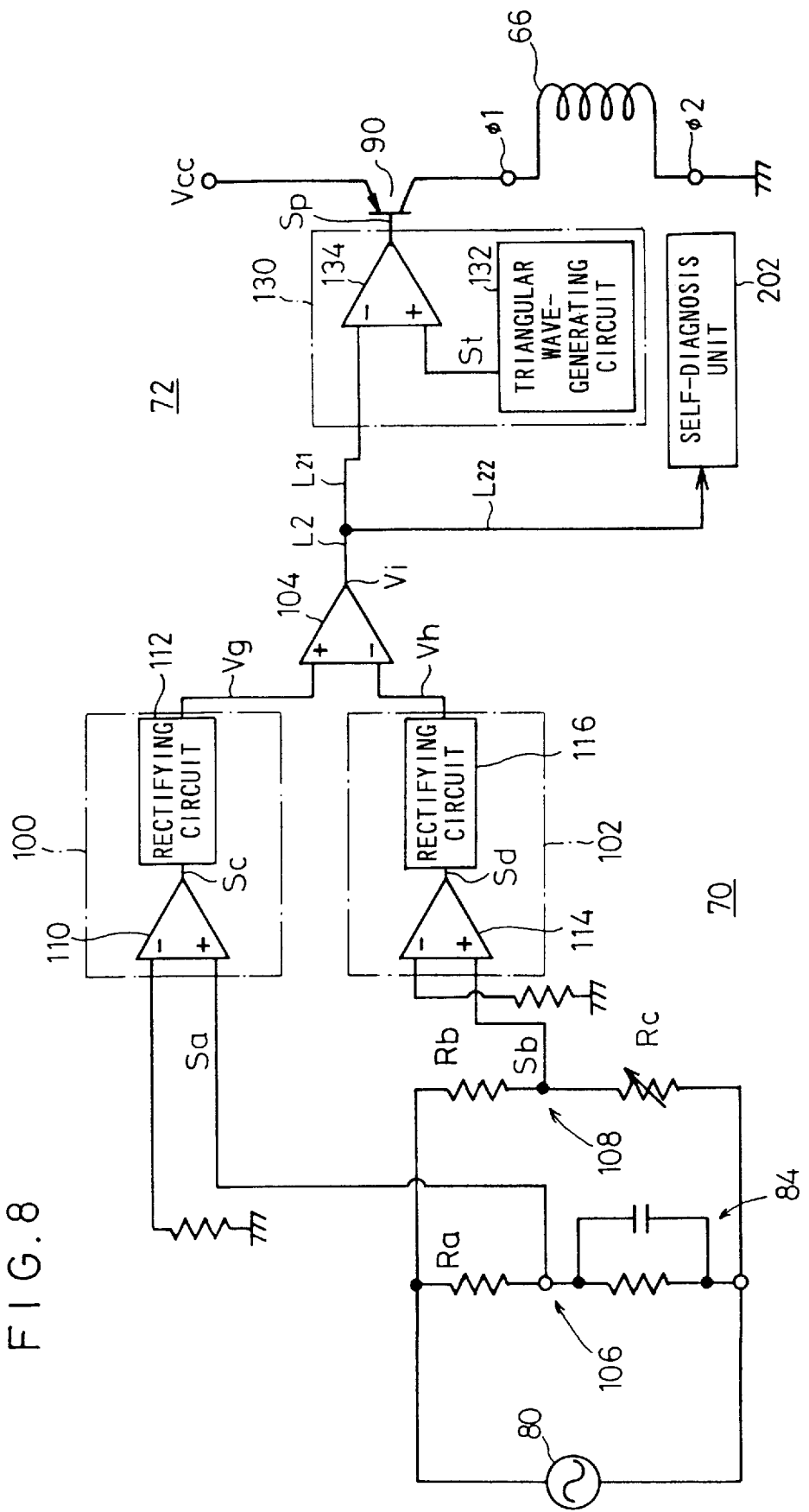
FIG. 8 shows a circuit diagram illustrating a first modified embodiment of the gas sensor according to the first embodiment, especially illustrating an arrangement of a heater control system.

That is, as shown in FIG. 8, the heater control system comprises the alternating current-generating circuit 80 as well as two detection circuits (first and second detection circuits 100, 102), a differential amplifier 104, and a pulse width-modulating circuit 130 for modulating the pulse width of the signal (hereinafter simply referred to as "base-driving signal Sp") for driving the base of the power transistor 90.

Specifically, at first, a first series circuit 106 comprising a fixed resistor Ra connected in series to the parallel circuit 84 including the resistor R and the capacitor C (the equivalent circuit of the impedance measurement objective constructed by the inner pumping electrode 22, the auxiliary pumping electrode 50, and the second solid electrolyte layer 10f disposed therebetween), and a second series circuit 108 comprising a fixed resistor Rb connected in series to a variable resistor Rc are connected in parallel between the supply line of the alternating current-generating circuit 80 respectively. The wiring connection is made such that an alternating current signal Sa, which is generated in the parallel circuit (element impedance) 84 by supplying the alternating current to the first and second series circuits 106, 108, is supplied to the first detection circuit 100. The wiring connection is made such that an alternating current signal Sb, which is generated in the variable resistor Rc, is supplied to the second detection circuit 102. Further, the wiring connection is made such that both of an output Vg of the first detection circuit 100 and an output Vh of the second detection circuit 102 are supplied to the differential amplifier 104 disposed at the downstream stage. FIG. 8 shows an example of wiring connection in which the output Vg of the first detection circuit 100 is inputted into a non-inverting input terminal of the differential amplifier 104, and the output Vh of the second detection circuit 102 is inputted into an inverting input terminal thereof.

The resistance value of the variable resistor Rc is set to be a resistance value corresponding to a normal impedance between the electrodes of the impedance measurement objective which is connected as the first series circuit 106. In this embodiment, the resistance value is set to be a resistance value corresponding to a normal impedance between the inner pumping electrode 22 and the auxiliary pumping electrode 50.

The first detection circuit 100 comprises, in connection, a non-inverting amplifying circuit 110 for amplifying, with a predetermined gain, the alternating current signal Sa generated in the parallel circuit (element impedance) 84, and a rectifying circuit 112 for rectifying an output Sc from the non-inverting amplifying circuit 110 and converting an obtained result into the voltage signal Vg at a direct current level corresponding to the output level. The second detection circuit 102 comprises, in connection, a non-inverting amplifying circuit 114 for amplifying, with a predetermined gain, the alternating current signal Sb generated in the variable resistor Rc, and a rectifying circuit 116 for rectifying an output Sd from the non-inverting amplifying circuit 114 and converting an obtained result into the voltage signal Vh at a direct current level corresponding to the output level. The fixed resistor Ra has the same resistance value as that of the fixed resistor Rb.

The pulse width-modulating circuit 130 comprises a triangular wave-generating circuit 132 for generating and outputting a predetermined triangular wave St having, for example, a bottom level of −5 V and an apex level of +5 V, and a comparator 134 for comparing the triangular wave St supplied from the triangular wave-generating circuit 132 with an output signal Vi supplied from the differential amplifier 104. FIG. 8 shows an example of wiring connection in which the output signal Vi supplied from the differential amplifier 104 is inputted into an inverting input terminal of the comparator 134, and the triangular wave St supplied from the triangular wave-generating circuit 132 is inputted into a non-inverting input terminal thereof.

Figure 9A:
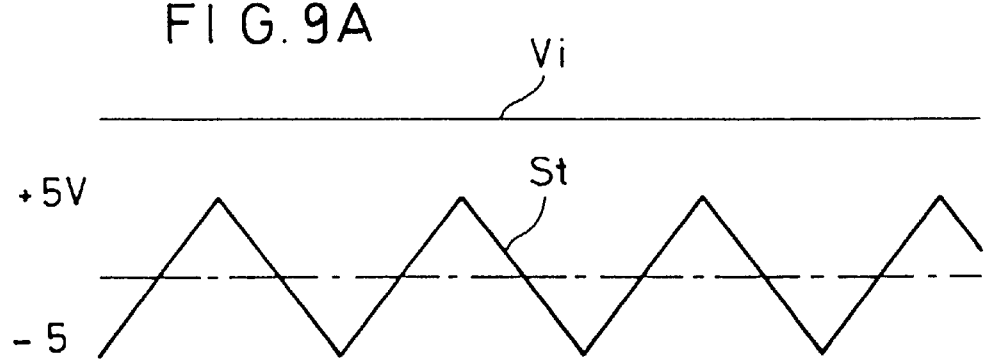
FIG. 9A shows a waveform illustrating a case in which the level of a deviation signal is higher than the apex level of the triangular wave.
Figure 9B:
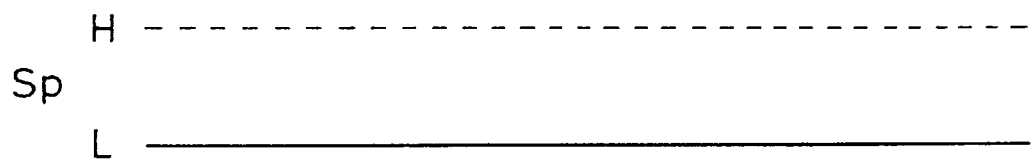
FIG. 9B shows a waveform illustrating a base-driving signal obtained under the condition shown in FIG. 9A.
Figure 10A:
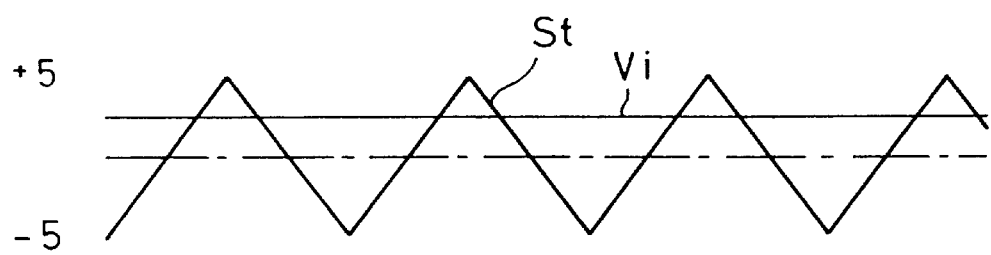
FIG. 10A shows a waveform illustrating a case in which the level of a deviation signal is between the middle point level and the apex level of the triangular wave.
Figure 10B:
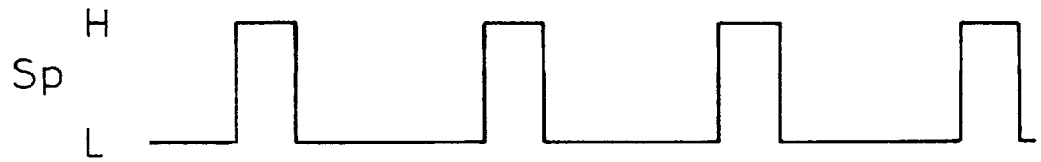
FIG. 10B shows a waveform illustrating a base-driving signal obtained under the condition shown in FIG. 10A.
Figure 11A:
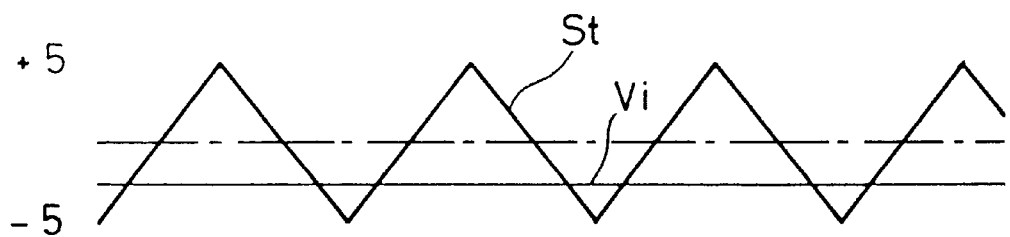
FIG. 11A shows a waveform illustrating a case in which the level of a deviation signal is between the bottom level and the middle point level of the triangular wave.
Figure 11B:
FIG. 11B shows a waveform illustrating a base-driving signal obtained under the condition shown in FIG. 11A.
Figure 12A:
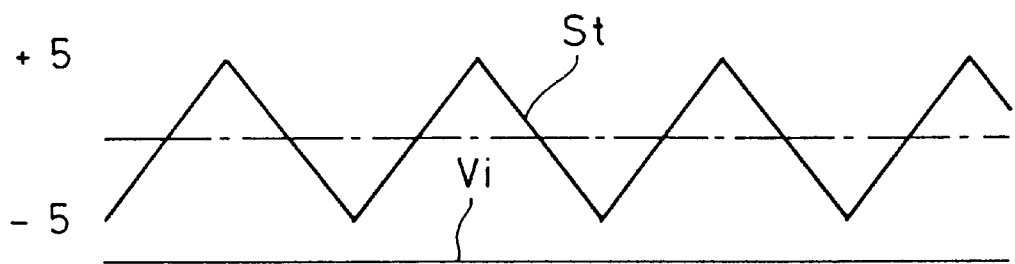
FIG. 12A shows a waveform illustrating a case in which the level of a deviation signal is lower than the bottom level of the triangular wave.
Figure 12B:
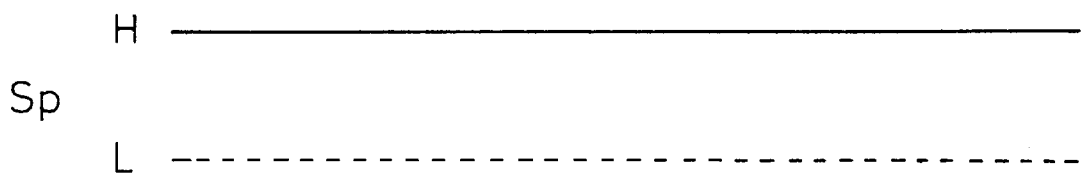
FIG. 12B shows a waveform illustrating a base-driving signal obtained under the condition shown in FIG. 12A.

The level of the output signal Vi from the differential amplifier 104 provides a threshold value for the triangular wave St. That is, if the level of the output signal Vi is not lower than the apex level of the triangular wave as shown in FIG. 9A, the base-driving signal at a low level is always outputted from the comparator 134 as shown in FIG. 9B. If the level of the output signal Vi is higher than the bottom level of the triangular wave and lower than the apex level as shown in FIGS. 10A and 11A, then the base-driving signal is outputted at a high level during a period in which the triangular wave St is higher than the level of the output signal Vi, and the base-driving signal is outputted at a low level during a period in which the triangular wave St is lower than the level of the output signal Vi, as shown in FIGS. 10B and 11B. If the level of the output signal Vi is not higher than the bottom level of the triangular wave as shown in FIG. 12A, the base-driving signal at a high level is always outputted from the comparator 134 as shown in FIG. 12B.

Next, the operation of the gas sensor according to the first modified embodiment, especially the operation of the heater control system will be explained. At first, the alternating current is supplied to the first series circuit 106 including the impedance measurement objective (parallel circuit) 84 by the aid of the alternating current-generating circuit 80, simultaneously with which the alternating current is also supplied to the second series circuit 108 including the variable resistor Rc set to have the resistance value corresponding to the normal impedance between the electrodes 22, 50.

When the alternating current is supplied to the first series circuit 106, the alternating current signal Sa generated in the parallel circuit 84 (element impedance) is supplied to the first detection circuit 100, and it is outputted after being converted into the direct current voltage signal Vg. On the other hand, when the alternating current is supplied to the second series circuit 108, the alternating current signal Sb generated in the variable resistor Rc is supplied to the second detection circuit 102, and it is outputted after being converted into the direct current voltage signal (reference signal) Vh.

Both of the voltage signal Vg outputted from the first detection circuit 100 and the reference signal Vh outputted from the second detection circuit 102 are supplied to the differential amplifier 104. The differential amplifier 104 determines a difference between the voltage signal Vg and the reference signal Vh to make an output as the deviation signal Vi.

The deviation signal Vi outputted from the differential amplifier 104, especially its voltage level is compared with the triangular wave St supplied from the triangular wave-generating circuit 132, by the aid of the comparator 134 included in the pulse width-modulating circuit 130 disposed at the downstream stage.

At first, during the warming-up period, the difference in temperature between the sensor element temperature and the measurement gas temperature is extremely large, and the impedance between the electrodes 22, 50 is extremely large. Accordingly, as shown in FIG. 9A, the level of the deviation signal Vi exceeds the apex level of the triangular wave St, and the base-driving signal Sp is always at a low level. As a result, the power transistor 90 is always turned ON, and the electric power is continuously applied to the heater 66. When the sensor element temperature is raised by the continuous electric power application to the heater 66, the level of the deviation signal Vi is lower than the apex level of the triangular wave St. Accordingly, the level of the deviation signal Vi varies within a range between the bottom level and the apex level depending on the high or low temperature of the measurement gas (see FIGS. 10A to 11B).

When the measurement gas temperature becomes lower than the predetermined temperature, and the impedance between the electrodes 22, 50 is increased, then the level of the deviation signal Vi outputted from the differential amplifier 104 of the impedance-detecting circuit 70 is also increased as shown in FIGS. 10A and 10B, and the width of the low level pulse of the base-driving signal Sp is widened in a degree corresponding to the foregoing increase. As a result, the period of time to apply the electric power to the heater 66 is prolonged, and the measurement gas temperature in the sensor element is gradually raised.

On the other hand, when the measurement gas temperature becomes higher than the predetermined temperature, and the impedance between the electrodes 22, 50 is decreased, then the level of the deviation signal Vi outputted from the differential amplifier 104 of the impedance-detecting circuit 70 is also decreased as shown in FIGS. 11A and 11B, and the width of the low level pulse of the base-driving signal Sp is narrowed in a degree corresponding to the foregoing decrease. As a result, the period of time to apply the electric power to the heater 66 is shortened, and the measurement gas temperature in the sensor element is gradually lowered.

As described above, the temperature in the sensor element can be maintained to be constant by controlling the electric power application to the heater 66 on the basis of the impedance value.

In the gas sensor according to the first modified embodiment, as shown in FIG. 8, the output line L2 of the differential amplifier 104 is branched into two. One output line $L_{21}$ is connected to the comparator 134, and the other output line $L_{22}$ is connected to the self-diagnosis unit 202. The self-diagnosis unit 202 is constructed in the same manner as the self-diagnosis unit 202 shown in FIG. 5 except that the signal, which is inputted into the self-diagnosis unit 202 through the other output line $L_{22}$, is the output signal Vi supplied from the differential amplifier 104. Accordingly, detailed explanation of the self-diagnosis unit 202 will be omitted.

Therefore, in the gas sensor according to the first modified embodiment, it is also possible to promptly and reliably detect whether or not the gas sensor is in a failure state at present. Therefore, it is possible to make quick response to maintain and manage the gas sensor.

Next, a gas sensor according to the second modified embodiment will be explained with reference to FIG. 13. The gas sensor according to the second modified embodiment is constructed in approximately the same manner as the gas sensor according to the first embodiment. However, the former is different from the latter in that a differential amplifier 118 is connected in place of the comparator 88 with hysteresis included in the heater control circuit 72. The power transistor 90 disposed at the downstream stage functions not as a digital switching circuit based on the use of the saturation region and the breaking region of the transistor, but as an analog current control circuit based on the use of the saturation region, the operating region, and the breaking region of the transistor.

That is, the gas sensor according to the second modified embodiment controls the measurement gas temperature in the sensor element by continuously controlling the amount of current supply on the basis of the change in impedance between the electrodes 22, 50 without stopping the electric power application to the heater 66. In this embodiment, it is possible to suppress excessive electric power consumption which would be otherwise observed upon the start of electric power application to the heater 66.

This embodiment illustrates wiring connection in which the deviation signal Vi from the differential amplifier 104 is supplied to the inverting terminal of the differential amplifier 118, and the reference level Ea is supplied to the non-inverting terminal thereof. In this process, the reference level Ea is set to be a level which is different from the reference level E shown in FIG. 4, because it is necessary to compare the reference level Ea with the level (deviation level) of the deviation signal Vi supplied from the differential amplifier 104. Specifically, the reference level Ea is set to be the same as the deviation level obtained when the measurement gas temperature in the sensor element is the predetermined temperature (desired temperature).

Figure 13:
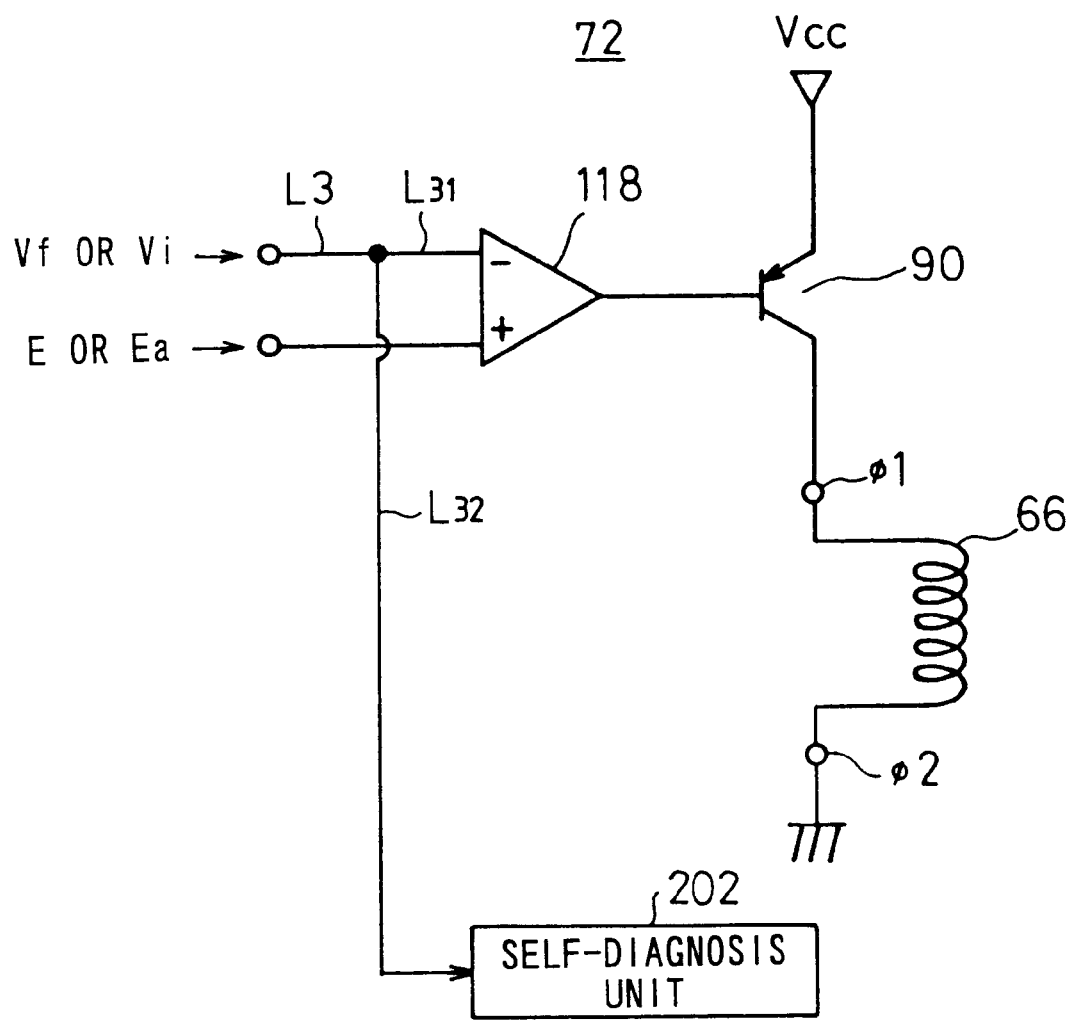
FIG. 13 shows a circuit diagram illustrating a second modified embodiment of the gas sensor according to the first embodiment, especially illustrating an arrangement of a heater control circuit of a heater control system.

In the gas sensor according to the second modified embodiment, as shown in FIG. 13, the input line L3 into the inverting input terminal of the differential amplifier 118 is branched into two. One output line $L_{31}$ is connected to the inverting input terminal, and the other output line $L_{32}$ is connected to the self-diagnosis unit 202. The self-diagnosis unit 202 is constructed in the same manner as the self-diagnosis unit 202 shown in FIG. 5 except that the signal, which is inputted into the self-diagnosis unit 202 through the other output line $L_{32}$, is the deviation signal Vi supplied from the differential amplifier 104 shown in FIG. 8. Accordingly, detailed explanation of the self-diagnosis unit 202 will be omitted.

Therefore, in the gas sensor according to the second modified embodiment, it is also possible to promptly and reliably detect whether or not the gas sensor is in a failure state at present. Therefore, it is possible to make quick response to maintain and manage the gas sensor.

Next, although not shown, a gas sensor according to the third modified embodiment is constructed such that the impedance-detecting circuit 70 for the heater control system is the impedance-detecting circuit included in the gas sensor 200A according to the first embodiment, i.e., the impedance-detecting circuit 70 based on the use of the filter circuit 86, and the heater control circuit 72 is the heater control circuit included in the gas sensor according to the second modified embodiment, i.e., the heater control circuit 72 based on the use of the differential amplifier 118.

The gas sensor according to the third modified embodiment is constructed such that the self-diagnosis unit 202 constructed in the same manner as the self-diagnosis unit 202 shown in FIG. 5 is connected to the other input line $L_{31}$ of the differential amplifier 118 shown in FIG. 13. Therefore, in the gas sensor according to this modified embodiment, it is also possible to promptly and reliably detect whether or not the gas sensor is in a failure state. Thus, it is possible to make quick response to maintain and manage the gas sensor.

Those constructed for the feedback control system 38 for the main pumping cell 26 is not limited to the feedback control system 38 shown in FIG. 2. It is also preferable to adopt a feedback control system 38 shown in FIG. 14.

That is, the feedback control system 38 includes a differential amplifier 120 for comparing a terminal voltage Vj between the reference electrode 32 and the inner pumping electrode 22 with a reference voltage Vr and amplifying an obtained difference with a predetermined gain to make an output, which is wired and connected such that the output voltage (differential voltage) from the differential amplifier 120 is applied, as the pumping voltage Vp1 to the main pumping cell 26, between the outer pumping electrode 24 and the inner pumping electrode 22. In this embodiment, the inner pumping electrode 22 is grounded.

Figure 14:
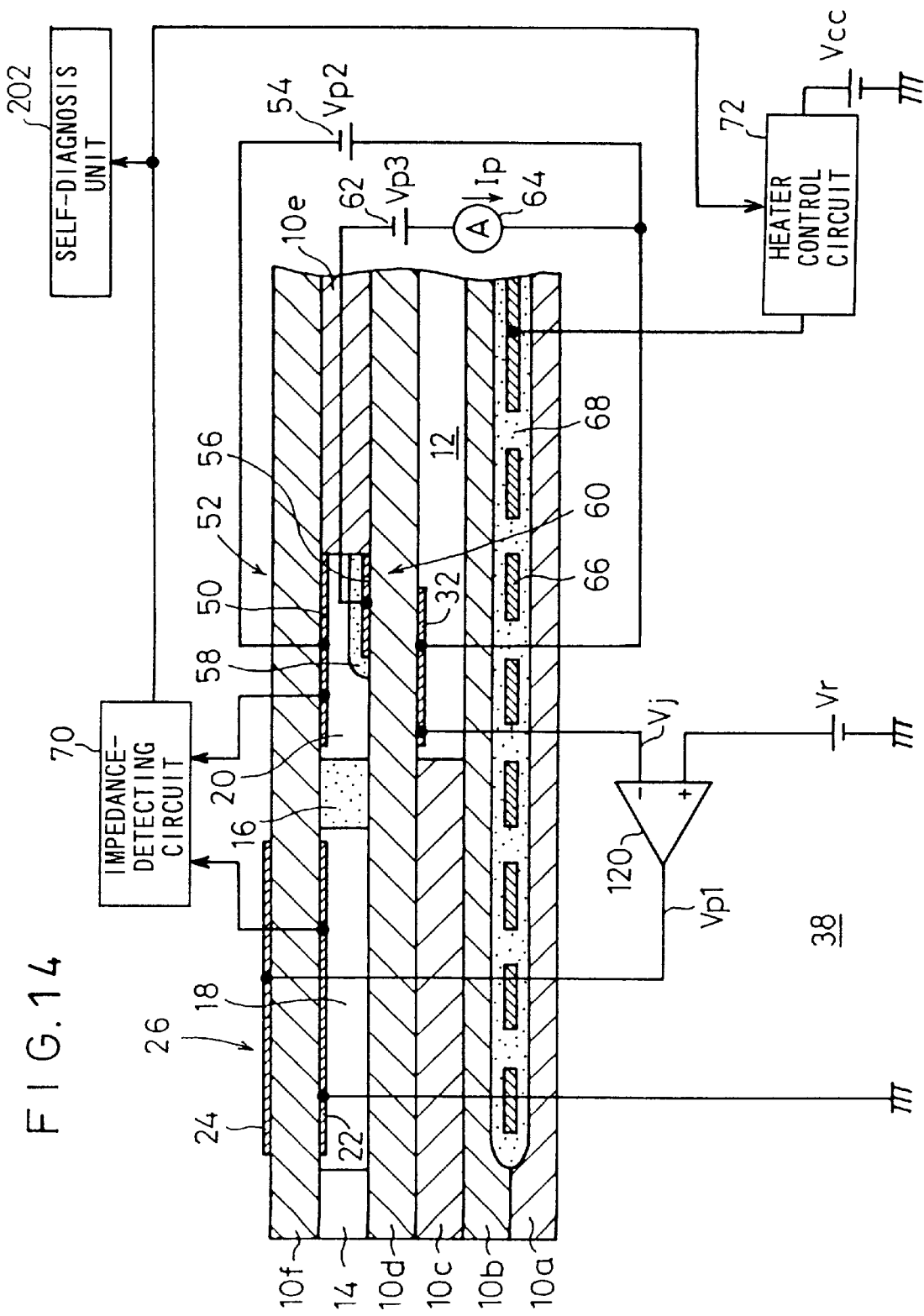
FIG. 14 shows a cross-sectional view illustrating another illustrative arrangement of a feedback control system for the main pumping cell of the gas sensor according to the first embodiment.

Next, the operation of the gas sensor shown in FIG. 14 will be explained. At first, the measurement gas is introduced into the first chamber 18 via the first diffusion rate-determining section 14. During this process, the terminal voltage Vj, which is obtained between the inner pumping electrode 22 of the main pumping cell 26 and the reference electrode 32 formed on the side of the reference gas-introducing space 12, is applied, for example, to the non-inverting terminal of the differential amplifier 120. The differential amplifier 120 determines the difference between the terminal voltage Vj supplied to the inverting terminal and the reference voltage Vr supplied to the non-inverting terminal. The voltage Vp1, which is obtained by amplifying the difference with the predetermined gain, is outputted from the output terminal of the differential amplifier 120. The output voltage Vp1 is applied to the outer pumping electrode 24 of the main pumping cell 26. However, in this embodiment, the inner pumping electrode 22 is allowed to have the ground electric potential (0 V). Consequently, the voltage between the both electrodes 22, 24 of the main pumping cell 26 is equivalent to the output voltage Vp1 from the differential amplifier 120.

Therefore, the main pumping cell 26 functions as a pump for pumping out or pumping in the oxygen contained in the measurement gas introduced into the first chamber 18 in an amount corresponding to the level of the output voltage Vp1. The oxygen concentration in the first chamber 18 is feedback-controlled to arrive at a predetermined level by repeating the foregoing series of operations.

In this embodiment, the terminal voltage (measured voltage) Vj, which is applied to the inverting terminal of the differential amplifier 120, is the terminal voltage between the inner pumping electrode 22 of the main pumping cell 26 and the reference electrode 32 disposed in the reference gas-introducing space 12. Accordingly, when the amount of oxygen pumped out by the main pumping cell 26 is changed, and the concentration of oxygen in the first chamber 18 is changed, then the terminal voltage between the inner pumping electrode 22 of the main pumping cell 26 and the reference electrode 32 is changed without any time delay (changed in real-time). Therefore, it is possible to effectively suppress the oscillation phenomenon which would be otherwise caused in the feedback control system 38.

In the feedback control system 38 described above, the control voltage (output voltage Vp1) is feedback-controlled so that the terminal voltage Vj between the inner pumping electrode 22 and the reference electrode 32 is converged to the same level as that of the reference voltage Vr.

In the gas sensor 200A according to the first embodiment (including the several modified embodiments), the impedance-detecting circuit 70 is used to detect the impedance between the inner pumping electrode 22 and the auxiliary pumping electrode 50 so that the measurement gas temperature in the sensor element is controlled. Further, the self-diagnosis unit 202 is used to judge whether or not the gas sensor 200A has any trouble on the basis of the impedance. However, the measurement gas temperature in the sensor element may be controlled, and the self-diagnosis process may be performed by detecting the impedance between the following electrodes:

(1) between the outer pumping electrode 24 and the auxiliary pumping electrode 50;

(2) between the reference electrode 32 and the auxiliary pumping electrode 50;

(3) between the inner pumping electrode 22 and the detecting electrode 56;

(4) between the outer pumping electrode 24 and the detecting electrode 56;

(5) between the detecting electrode 56 and the reference electrode 32;

(6) between the inner pumping electrode 22 and the reference electrode 32; and (7) between the outer pumping electrode 24 and the reference electrode 32.

Especially, when the measurement gas temperature in the sensor element is controlled by detecting the impedance between the detecting electrode 56 through which the detection current Ip flows and the other electrode, it is possible to more accurately control the measurement gas temperature in the vicinity of the detecting electrode 56 in the sensor element. As a result, it is possible to effectively suppress the variation of the detection output (the pumping current value or the electromotive force) depending on the measurement gas temperature. Thus, it is possible to realize improvement in detection accuracy and improvement in reliability of the gas sensor 200A.

Figure 16:
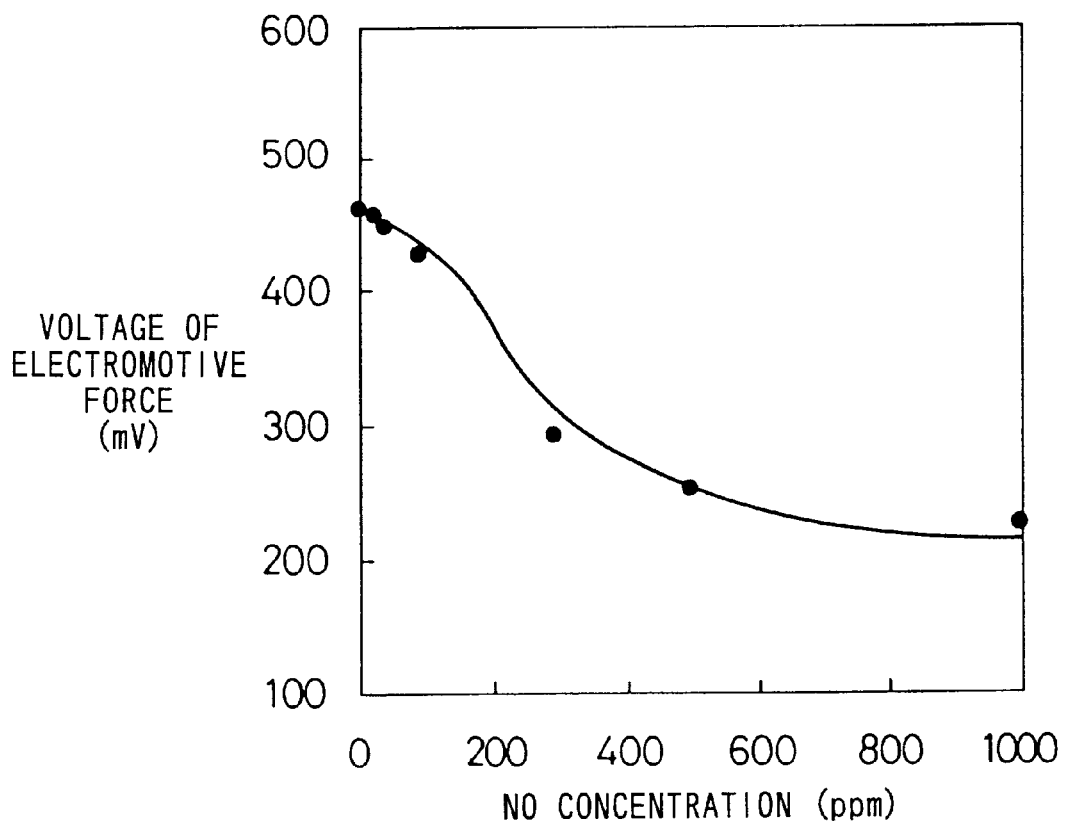
FIG. 16 shows a characteristic curve illustrating an output characteristic of the gas sensor according to the second embodiment.
Figure 17:
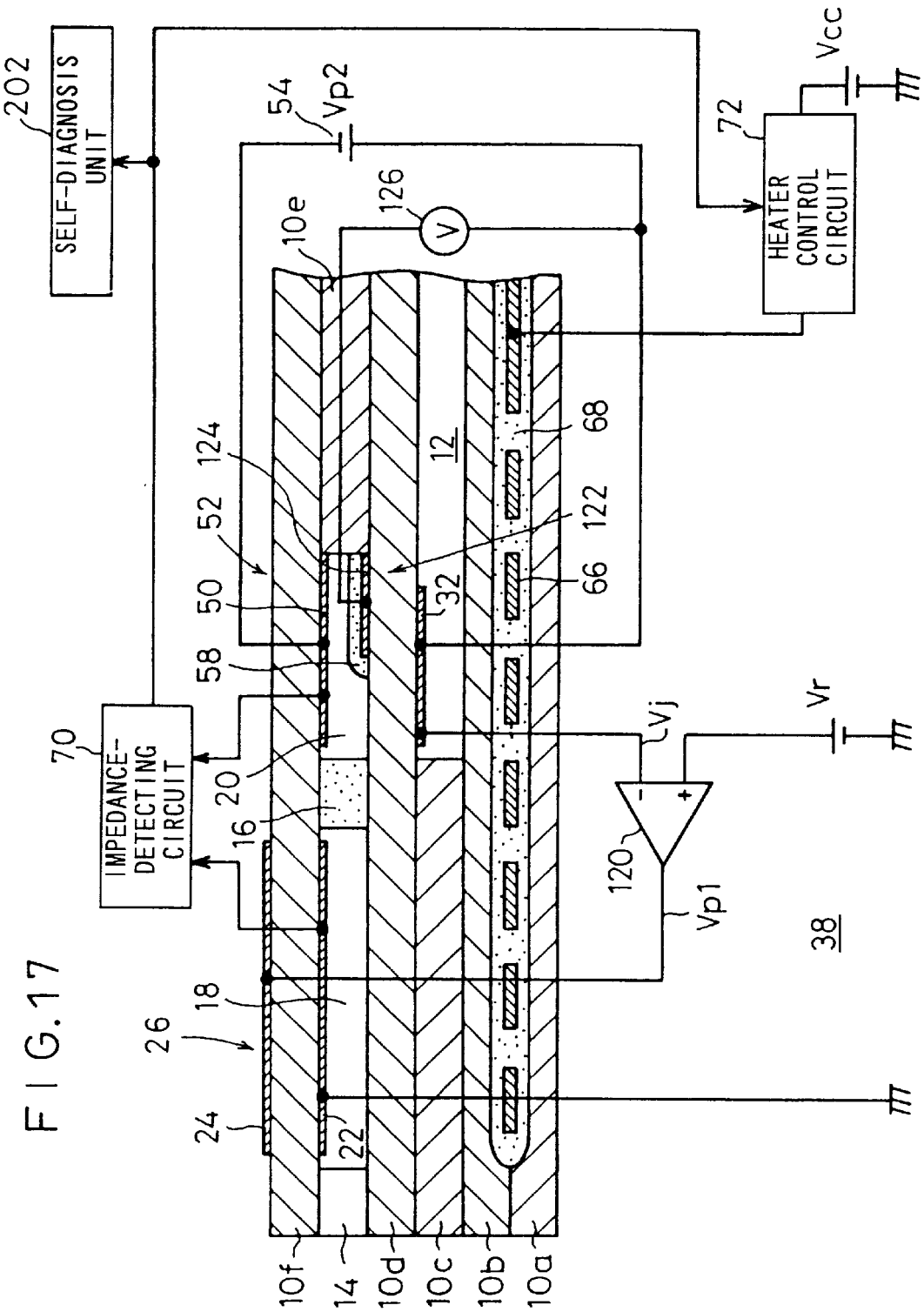
FIG. 17 shows a cross-sectional view illustrating another illustrative arrangement of a feedback control system for a main pumping cell of the gas sensor according to the second embodiment.

Next, a gas sensor 200B according to the second embodiment will be explained with reference to FIGS. 15 to 17. Components or parts corresponding to those shown in FIG. 1 are designated by the same reference numerals, duplicate explanation of which will be omitted.

Figure 15:
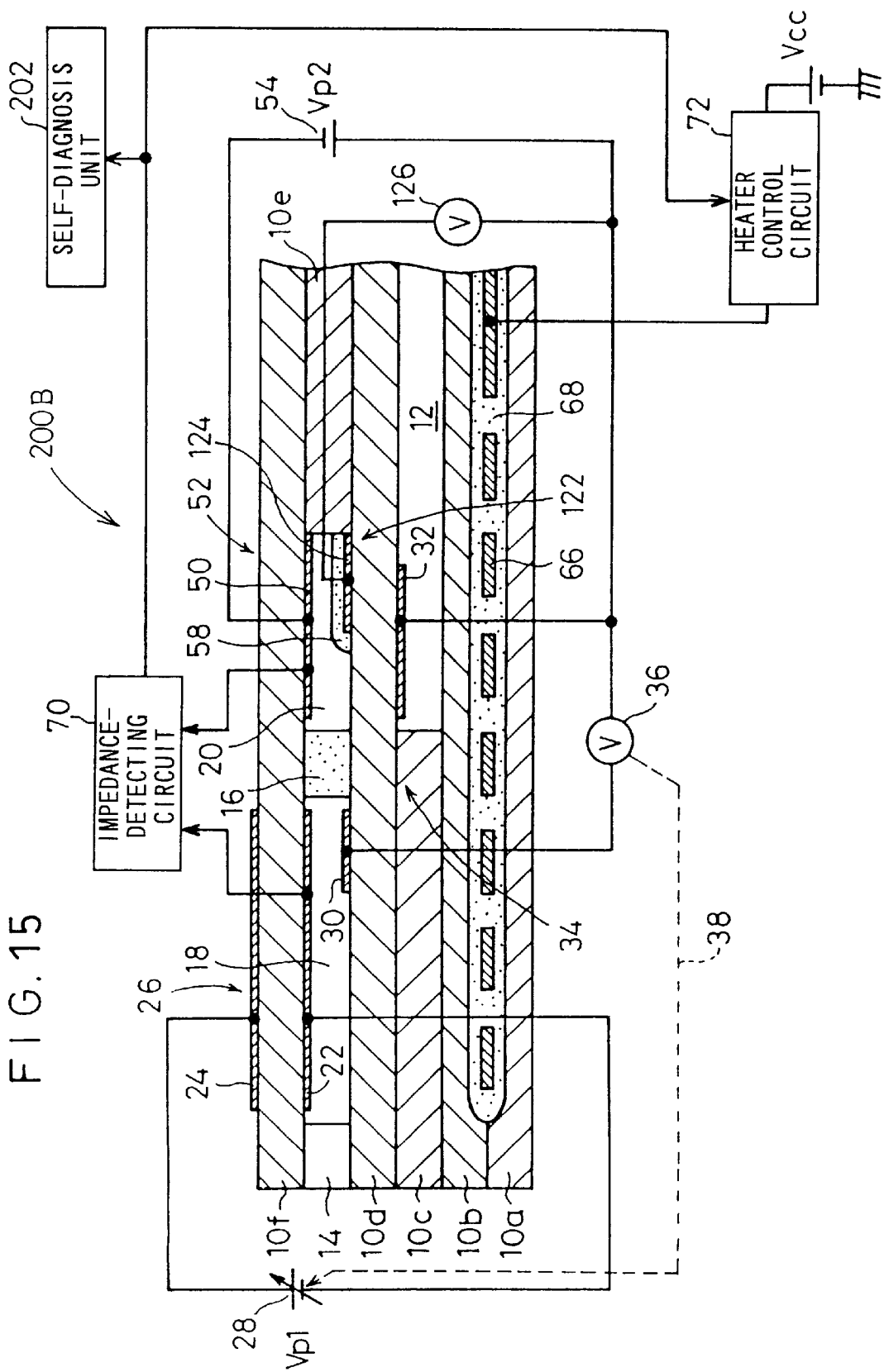
FIG. 15 shows a cross-sectional view illustrating a gas sensor according to a second embodiment.

As shown in FIG. 15, the gas sensor 200B according to the second embodiment is constructed in approximately the same manner as the gas sensor 200A according to the first embodiment. However, the former is different from the latter in that an oxygen partial pressure-detecting cell 122 is provided in place of the measuring pumping cell 60.

The oxygen partial pressure-detecting cell 122 comprises a detecting electrode 124 formed on the upper surface portion for forming the second chamber 20, of the upper surface of the first solid electrolyte layer 10$d$, the reference electrode 32 formed on the lower surface of the first solid electrolyte layer 10$d$, and the first solid electrolyte layer 10$d$ interposed between the both electrodes 124, 32.

In this embodiment, an electromotive force (electromotive force of the oxygen concentration cell), which corresponds to the difference in oxygen concentration between the atmosphere around the detecting electrode 124 and the atmosphere around the reference electrode 32, is generated between the detecting electrode 124 and the reference electrode 32 of the oxygen partial pressure-detecting cell 122. Therefore, the partial pressure of oxygen in the atmosphere around the detecting electrode 124, in other words, the partial pressure of oxygen defined by the oxygen produced by reduction or decomposition of the measurement gas component (NOx) is detected as a voltage value by measuring the electromotive force generated between the detecting electrode 124 and the reference electrode 32 by using a voltmeter 126.

Now, the principle of detection performed by the gas sensor 200B according to the second embodiment will be explained with reference to a characteristic curve shown in FIG. 16.

At first, when the NO concentration in the external space is 0 ppm, if the oxygen concentration in the atmosphere in the first chamber 18 is controlled by the aid of the feedback control system 38 so that the pumping voltage Vp1 for the main pumping cell 26 has a value ($10^{-7}$ atm) corresponding to 300 mV, then the oxygen concentration in the atmosphere in the second chamber 20 is also $10^{-7}$ atm. Thus, the electromotive force, which is generated between the detecting electrode 124 and the reference electrode 32 of the oxygen partial pressure-detecting cell 122 provided for the second chamber 20, is about 460 mV.

When the NO concentration in the external space is gradually increased, then the reducing or decomposing reaction of NO is caused on the detecting electrode 124, and the oxygen concentration in the atmosphere around the detecting electrode 124 is increased, because the detecting electrode 124 also functions as a NOx-reducing catalyst in the same manner as the detecting electrode 56 of the measuring pumping cell 60 described above (see FIG. 1). Accordingly, the electromotive force, which is generated between the detecting electrode 124 and the reference electrode 32, is gradually decreased. With reference to FIG. 16 illustrating the characteristic curve, for example, when the NO concentration increases to 300 ppm, 500 ppm, and 1000 ppm, the electromotive force detected by the voltmeter 126 is gradually decreased to 300 mV, 250 mV, and 220 mV respectively.

The degree of the decrease in electromotive force represents the NO concentration. In other words, the electromotive force, which is outputted from the oxygen partial pressure-detecting cell 122 for the second chamber 20, constructed by the detecting electrode 124, the reference electrode 32, and the first solid electrolyte layer 10d, represents the NO concentration in the measurement gas.

The gas sensor 200B according to the second embodiment also includes the self-diagnosis unit 202 and the heater control system (the impedance-detecting circuit 70 and the heater control circuit 72) in the same manner as the heater control system of the gas sensor 200A according to the first embodiment (including the several modified embodiments).

Therefore, in the gas sensor 200B according to the second embodiment, it is unnecessary to manufacture the gas sensor as having a strict resistance ratio between the resistance value of the heater lead section and the resistance value of the heat-generating section of the heater, in the same manner as the gas sensor 200A according to the first embodiment. Moreover, it is possible to avoid the influence of the temperature of the measurement gas, which would be otherwise exerted due to the increase in resistance value of the heater lead section.

In another viewpoint, the impedance value between the inner pumping electrode 22 and the auxiliary pumping electrode 50 is detected. Accordingly, the electromotive force, which is generated by the oxygen partial pressure-detecting cell 122, is free from variation which would be otherwise caused due to the detection of the impedance. Thus, it is possible to suppress, for example, superimposition of noise and fluctuation of the electromotive force (voltage) detected by the voltmeter 126. Therefore, it is possible to suppress variation in detection output which would be otherwise caused depending on the temperature of the measurement gas. Moreover, it is possible to realize a high S/N ratio of the detection output.

Further, the temperature of the measurement gas in the vicinity of the detecting electrode 124 can be highly accurately controlled, and the variation of the detection output (electromotive force), which would be otherwise caused by the temperature of the measurement gas, can be effectively suppressed. These advantages result in improvement in detection accuracy of the gas sensor and improvement in reliability.

The gas sensor 200B according to the second embodiment also includes the self-diagnosis unit 202 in the same manner as in the gas sensor 200A according to the first embodiment. Therefore, it is also possible to promptly and reliably detect whether or not the gas sensor 200B is in a failure state at present. Therefore, it is possible to make quick response to maintain and manage the gas sensor 200B.

In the gas sensor 200B according to the second embodiment, the impedance-detecting circuit 70 is used to detect the impedance between the inner pumping electrode 22 and the auxiliary pumping electrode 50 so that the measurement gas temperature in the sensor element is controlled. Further, the self-diagnosis unit 202 is used to judge whether or not the gas sensor 200B has any trouble on the basis of the impedance. However, the measurement gas temperature in the sensor element may be controlled, and the self-diagnosis process may be performed by detecting the impedance between the following electrodes:

(1) between the outer pumping electrode 24 and the auxiliary pumping electrode 50;

(2) between the reference electrode 32 and the auxiliary pumping electrode 50;

(3) between the inner pumping electrode 22 and the detecting electrode 124;

(4) between the outer pumping electrode 24 and the detecting electrode 124; and (5) between the detecting electrode 124 and the reference electrode 32.

The arrangement of the feedback control system 38 for the main pumping cell 26 is not limited to the feedback control system shown in FIG. 2. Alternatively, as shown in FIG. 17, it is also preferable to adopt the same arrangement as that of the feedback control system 38 shown in FIG. 14. In this arrangement, an effect is obtained in that the oscillation phenomenon in the feedback control system 38 can be effectively suppressed.

The gas sensors 200A, 200B according to the first and second embodiments (including the several modified embodiments) adopt the self-diagnosis unit having the arrangement shown in FIG. 5. However, such an arrangement is persistently illustrative. The self-diagnosis unit can be constructed by a combination of a variety of digital circuits and analog circuits.

The self-diagnosis unit 202 described above detects the state of the gas sensor by monitoring the output from the final stage of the impedance-detecting circuit. However, various methods may be adopted, for example, the impedance itself of the sensor element may be monitored to compare it with a prescribed value.

The gas sensors according to the embodiments described above are directed to NOx as the measurement gas component. However, the present invention is also effectively applicable to the measurement of bound oxygen-containing gas components such as $H_2O$ and $CO_2$ other than NOx, in which the measurement is affected by oxygen existing in the measurement gas.

It is a matter of course that the present invention is not limited to the embodiments described above, which may be constructed in other various forms without deviating from the gist or essential characteristics of the present invention.

As explained above, according to the gas sensor concerning the present invention, it is possible to promptly and reliably detect whether or not the gas sensor is in a failure state at present, and it is possible to make quick response to maintain and manage the gas sensor.

What is claimed is:

1. A gas sensor comprising:
a main pumping means including an inner pumping electrode and an outer pumping electrode located inside and outside of a first chamber formed in a substrate comprised of solid electrolyte, for pumping-processing oxygen contained in a measurement gas introduced from an external space into said first chamber on the basis of a control voltage applied between said electrodes; and
an electric signal-generating conversion means including a detecting electrode and a reference electrode located inside and outside of a second chamber formed in said substrate, for making conversion into an electric signal corresponding to an amount of oxygen contained in said measurement gas after being pumping-processed by said main pumping means, wherein:
a measurement gas component contained in said measurement gas is measured on the basis of said electric signal supplied from said electric signal-generating conversion means, said gas sensor further comprising:
- a heater for heating at least said main pumping means and said electric signal-generating conversion means to predetermined temperatures;
- an impedance-detecting means for detecting an impedance between an electrode of said main pumping means and an electrode of said second chamber, said impedance detection means including an alternating current generating circuit for supplying an alternating current between said electrodes subjected to said impedance detection; and
- a self-diagnosis means for comparing an impedance value detected by said impedance-detecting means with a prescribed value to decide whether or not any trouble occurs, on the basis of a result of comparison.

2. The gas sensor according to claim 1, wherein:

said electric signal-generating conversion means includes a measuring pumping means for decomposing said measurement gas component contained in said measurement gas after being pumping-processed by said main pumping means, by means of catalytic action and/or electrolysis, and pumping-processing oxygen produced by said decomposition; and said measurement gas component contained in said measurement gas is measured on the basis of a pumping current flowing through said measuring pumping means in accordance with said pumping process effected by said measuring pumping means.

3. The gas sensor according to claim 2, wherein said impedance-detecting means detects said impedance between an electrode disposed for said main pumping means and an electrode disposed for said measuring pumping means.

4. The gas sensor according to claim 1, wherein:

said electric signal-generating conversion means comprises a concentration-detecting means for decomposing said measurement gas component contained in said measurement gas after being pumping-processed by said main pumping means, by means of catalytic action, and generating an electromotive force corresponding to a difference between an amount of oxygen produced by said decomposition and an amount of oxygen contained in a reference gas; and said measurement gas component contained in said measurement gas is measured on the basis of said electromotive force detected by said concentration-detecting means.

5. The gas sensor according to claim 4, wherein said impedance-detecting means detects said impedance between an electrode disposed for said main pumping means and an electrode disposed for said concentration-detecting means.

6. The gas sensor according to claim 1, wherein said self-diagnosis means judges that trouble occurs, when said impedance value detected by said impedance-detecting means does not arrive at said prescribed value for a predetermined period of time.

7. The gas sensor according to claim 6, wherein said self-diagnosis means comprises:
- a comparing means for comparing said impedance value detected by said impedance-detecting means with said prescribed value; and
- a monitoring means for temporarily or periodically monitoring a comparison output supplied from said comparing means and judging that trouble occurs, when said comparison output does not arrive at said prescribed value for a predetermined period of time.

8. The gas sensor according to claim 7, wherein said monitoring means monitors said comparison output supplied from said comparing means at intervals of a certain period of time for said predetermined period of time.

9. The gas sensor according to claim 7, wherein said monitoring means monitors said comparison output supplied from said comparing means for said predetermined period of time, upon completion of a predetermined condition.

10. The gas sensor according to claim 9, wherein said monitoring means monitors said comparison output supplied from said comparing means at intervals of a certain period of time for said predetermined period of time.

* * * * *